United States Patent
Klett

(10) Patent No.: US 8,287,276 B2
(45) Date of Patent: Oct. 16, 2012

(54) METHOD AND DEVICE FOR THE TRANSFER OF A JAW MODEL IN RELATION TO A HINGE AXIS

(75) Inventor: Rolf Klett, Hoechberg (DE)

(73) Assignee: Dental Innovation GmbH, Dortmund (DE)

( * ) Notice: Subject to any disclaimer, the term of this patent is extended or adjusted under 35 U.S.C. 154(b) by 330 days.

(21) Appl. No.: 12/312,941

(22) PCT Filed: Nov. 29, 2007

(86) PCT No.: PCT/DE2007/002161
§ 371 (c)(1),
(2), (4) Date: Jun. 1, 2009

(87) PCT Pub. No.: WO2008/064666
PCT Pub. Date: Jun. 5, 2008

(65) Prior Publication Data
US 2010/0075274 A1    Mar. 25, 2010

(30) Foreign Application Priority Data
Dec. 1, 2006   (DE) .......................... 10 2006 057 220

(51) Int. Cl.
*A61C 11/00*    (2006.01)
(52) U.S. Cl. .......................................... 433/54; 433/73
(58) Field of Classification Search .................... 433/54, 433/57, 68, 70, 73
See application file for complete search history.

(56) References Cited

U.S. PATENT DOCUMENTS

| | | | | |
|---|---|---|---|---|
| 3,200,497 A | * | 8/1965 | Goodfriend | 433/44 |
| 4,695,252 A | * | 9/1987 | Edwardson | 433/73 |
| 4,892,480 A | * | 1/1990 | Levandoski | 433/73 |
| 5,090,901 A | * | 2/1992 | Levandoski | 433/56 |
| 5,632,619 A | * | 5/1997 | Polz | 433/57 |
| 6,120,290 A | | 9/2000 | Fukushima et al. | |
| 2007/0292004 A1 | | 12/2007 | Peters | |

FOREIGN PATENT DOCUMENTS

| | | |
|---|---|---|
| DE | 43 17 532 | 12/1994 |
| DE | 44 11 907 | 10/1995 |
| DE | 199 56 876 | 5/2001 |
| DE | 10 2006 004 197.6 | 8/2007 |
| WO | WO 2004/029903 | 4/2004 |
| WO | WO 2006/015809 | 2/2006 |

OTHER PUBLICATIONS

International Search Report, PCT/DE2007/002161 (Jan. 8, 2008).

* cited by examiner

*Primary Examiner* — Ralph Lewis
(74) *Attorney, Agent, or Firm* — Collard & Roe, P.C.

(57) ABSTRACT

The invention relates to a method and a registering system for the transfer of a jaw model in relation to a hinge axis, for example, in an articulator, and to a connection device for connecting a lower jaw adapter (1) to a measuring carrier (4), and a bite carrier (3) for producing a bite key. The invention is characterized in that the transfer of the mandibular joint geometry, especially the exact position of the hinge axis of the patient, can be carried out in a state of assembly or an articulator using only a hinge axis determination relative to the lower jaw of the patient. The transfer of the facial arc required until now in prior art is rendered superfluous by the invention. Moreover, the possibilities of use of the transfer in relation to the hinge axis are extended, modularised and simultaneously simplified and accelerated. Sources of error are eliminated, the expenditure on equipment and costs of the transfer of the model can be critically reduced.

18 Claims, 7 Drawing Sheets

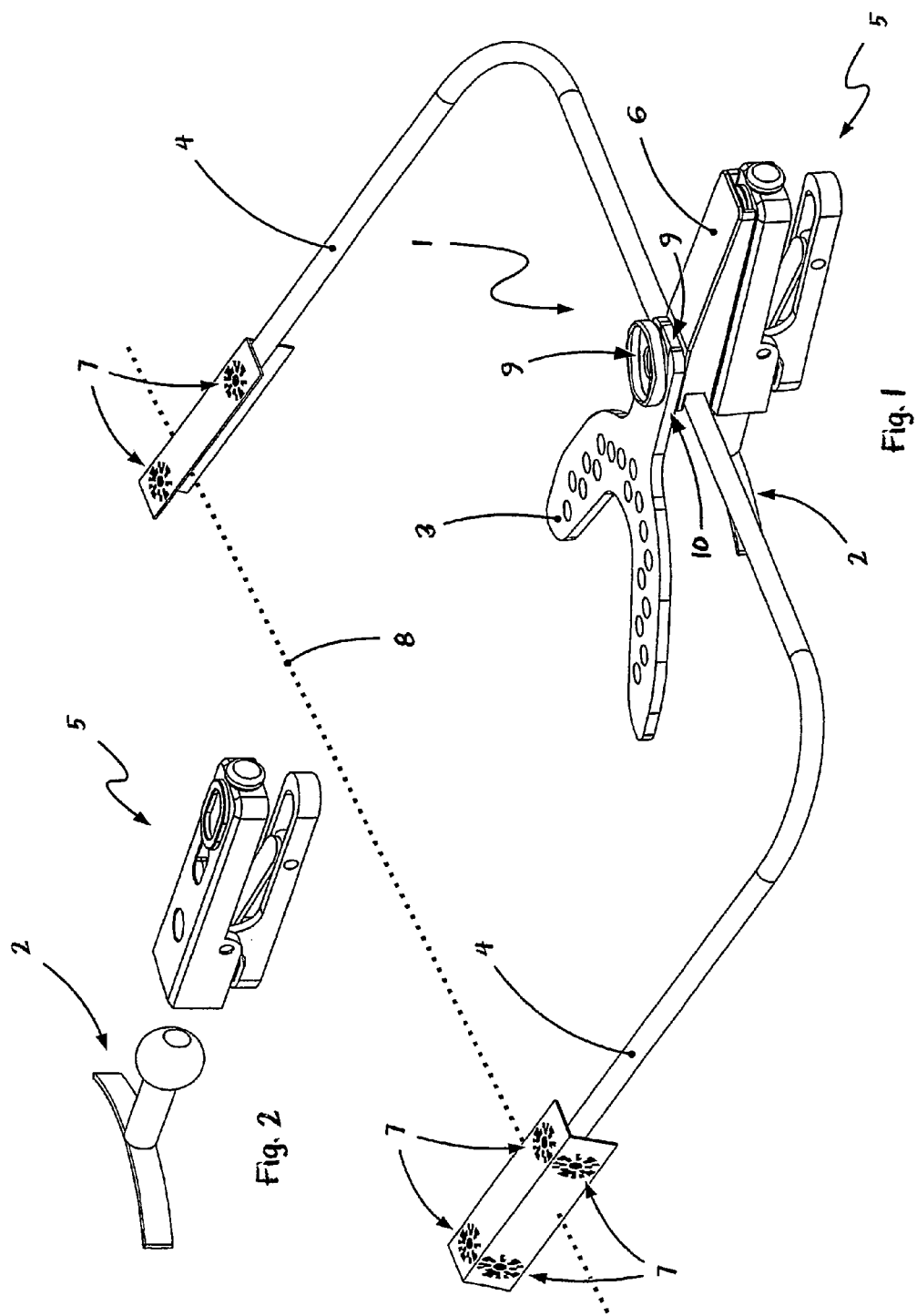

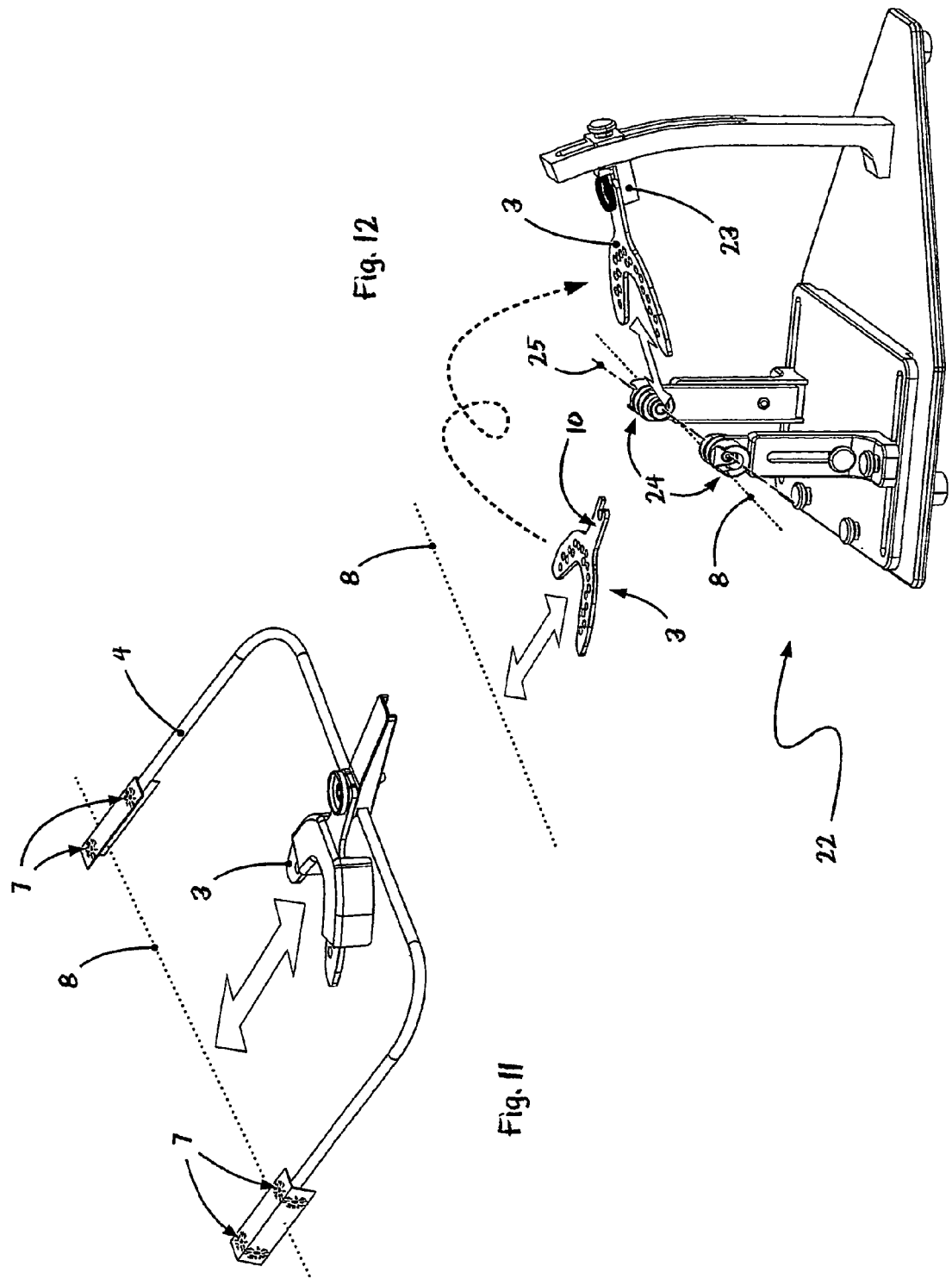

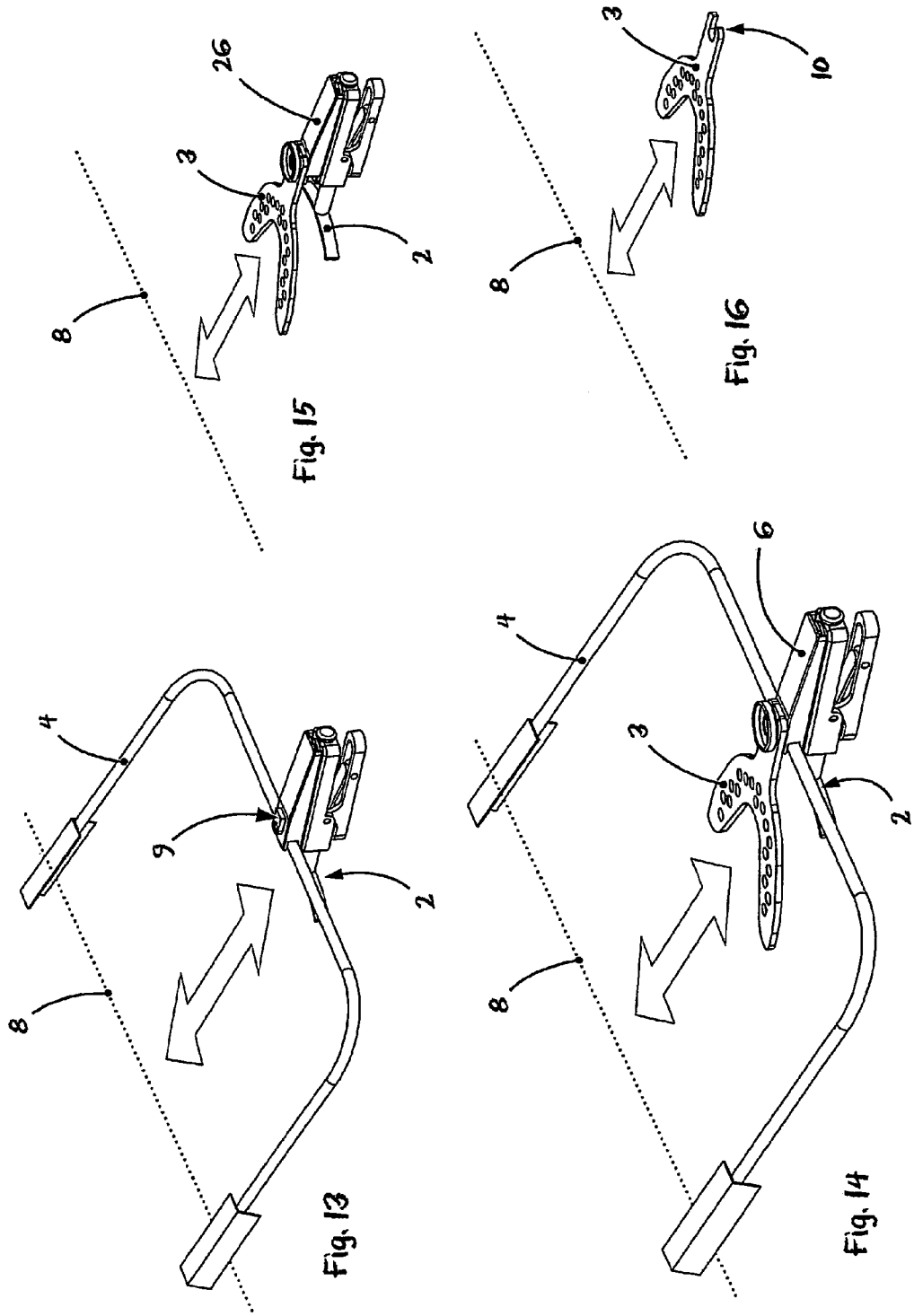

METHOD AND DEVICE FOR THE TRANSFER OF A JAW MODEL IN RELATION TO A HINGE AXIS

CROSS REFERENCE TO RELATED APPLICATIONS

This application is the National Stage of PCT/DE2007/002161 filed on Nov. 29, 2007, which claims priority under 35 U.S.C. §119 of German Application No. 10 2006 057 220.3 filed on Dec. 1, 2006. The international application under PCT article 21(2) was not published in English.

BACKGROUND OF THE INVENTION

1. Field of the Invention

The invention relates to a method for transfer of a jaw model of a patient in relation to a hinge axis, a registration system for performing the method, a connection device for connecting a lower jaw adapter with a measurement carrier, as well as a bite carrier.

2. The Prior Art

Frequently, dental-technology work, such as preparation, production, and adaptation of tooth replacements, production of inlays or occlusal splints, etc., can be carried out only in part on the patient, i.e. in the patient's mouth itself, and instead must take place, at least to a significant part, in the dental technology laboratory, for example, in an articulator. In this connection, the articulator has the task of more or less precisely replicating the geometric conditions in the region of the patient's jaw, i.e. of simulating them at the work place of the dental technician.

In the sense of the quality and the required precision of dental technology work, which frequently lies in the range of hundredths of a millimeter or even less because of the great sensory sensitivity of the gnathological system in humans, it can become necessary in this connection—depending on the complexity of the work to be performed—to very precisely model the patient's chewing apparatus and its geometric characteristic values in the dental technology articulator.

These fundamental geometric characteristic values of the jaw geometry that must be transferred to the articulator include, in particular—but by no means exclusively—the spatial relative positions of the rows of teeth in the upper jaw and the lower jaw with regard to one another, as well as with regard to the patient's hinge axis, in other words the joint axis of the lower jaw with reference to the upper jaw or skull, respectively. Since these geometric characteristic values are different for every patient, the so-called average value settings of these geometric characteristic values, particularly an average setting of the hinge axis position on the articulator, can at most be used for dental technology work that sets only low precision requirements.

For more demanding dental technology work, however, it is usually absolutely necessary to reproduce the gnathological geometry of patients, and, in this connection, particularly the spatial relative position of the jaw with regard to the patient's hinge axis, with the greatest possible precision, in the articulator.

Reproduction of the geometric conditions at the jaw of a patient in an articulator usually takes place, in this connection, in that a model of a first row of teeth of the patient is mounted in an articulator, by means of corresponding transfer methods or transfer devices, with the correct position and location with reference to the hinge axis of the articulator. Subsequently, a model of the second row of teeth of the patient, in the occluded position relative to the first row of teeth, is also positioned in the articulator—this usually takes place by means of a centered registration, in other words using an impression of both rows of the patient's teeth in the occluded position, in a suitably thin impression material—and then the model of the second row of teeth, in this occluded position, is also attached to the articulator. In this manner, the relative position of the two rows of the patient's teeth with regard to one another, as well as with regard to the hinge axis of the patient, i.e. also with regard to the articulator hinge axis, is reproduced in the articulator.

In the methods and devices known from the state of the art for the transfer of jaw models of a patient, transfer of the geometric relative relationships between jaw and hinge axis that are present at the patient's skull, to the dental technology articulator, i.e. to an articulator assembly stand, generally takes place by means of a facial arc. In this connection, the facial arc serves to store the spatial relative position of a row of the patient's teeth, with regard to the hinge axis of the patient, in most cases in mechanical manner, i.e. to code it by means of corresponding adjustment of the facial arc, in such a manner that this spatial relative position between the row of teeth and the hinge axis of the patient can also be reproduced later, outside of the patient, particularly in the dental technology laboratory, i.e. on the articulator.

For this purpose, in the state of the art, the spatial relative position between the row of teeth of the upper jaw, on the one hand, and certain fixed points on the patient's skull, on the other hand, is generally recorded by means of corresponding adjustment of the facial arc, i.e. therefore coded in the facial arc. In this connection, the so-called arbitrary facial arc transfer known from the state of the art, on the one hand, usually makes use of an empirically determined relationship between the typical location of the hinge axis relative to the patient's porion—in other words relative to the highest point of the external auditory meatus—on the human skull.

In this known arbitrary facial arc transfer, it is therefore not the actual hinge axis that is recorded on the patient's skull and coded by means of the facial arc, for transfer to the articulator, but rather—for example by means of corresponding ear olives disposed on the facial arc that are introduced into the external auditory meatus of the patient—a conclusion is drawn from the position of the porion to the location of the patient's hinge axis, merely on the basis of statistical average values.

The arbitrary facial arc transfer can therefore only guarantee an average reproduction, but by no means a precise reproduction of the geometrical conditions of the gnathological system of a patient in the articulator, and is therefore also suited only for use in less demanding work in the dental technology laboratory, in which the main point of importance is reproduction of the correct occlusion between upper jaw and lower jaw, which is undertaken by means of a centered registration.

More demanding restoration work in the articulator, however, frequently requires not only an average transfer, but rather an individual and precise transfer of the hinge axis location relative to the rows of teeth of the patient's jaw. In the state of the art, the determination and transfer of the actual hinge axis location required for this generally take place on the basis of a kinematic determination of the patient's hinge axis. This kinematic hinge axis determination can be carried out electronically, for example using a lower jaw measurement arc—or by means of mechanical pin recording. In this connection, the actual patient hinge axis that is determined can subsequently be coded onto a so-called terminal facial arc, on which, in contrast to the arbitrary facial arc, the location of the hinge axis can be adjusted and thus individually transferred to the articulator.

However, in the state of the art, it is necessary, even in the case of a geometry transfer by means of kinematic axis determination and terminal facial arc, to first record the kinematically determined actual hinge axis location by means of corresponding measurement markings, mostly on the patient's skin. Subsequent to this, the apparatus used for axis localization is removed from the patient's head, the terminal facial arc is coupled with the row of teeth of the upper jaw, and the arc is adjusted to the previously applied joint axis measurement markings. However, since the patient's skin is easily movable relative to the patient's skull—and thus the measurement markings placed on the skin are easily movable with reference to the hinge axis location—this can already induce not insignificant transfer errors when using a terminal facial arc.

In every case, however—even independent of whether or not imprecisions are induced by means of easily displaceable measurement markings placed on the patient's skin—simply the double transfer process of the hinge axis measurement values first from the measurement arc to the measurement markings, and then the manual recording of the measurement markings by means of a facial arc, brings not insignificant error sources with it.

Only subsequent to the corresponding adjustment of the terminal facial arc—particularly using the markings relating to the hinge axis location on the patient's head—can the facial arc then be removed from the patient's head, and the gnathological geometry of the patient can be transferred to an articulator or an articulator assembly stand, by means of the spatial relative relationship between the row of teeth of the upper jaw and the kinematically determined condylar axis now stored in the facial arc.

In the end result, it must be stated, with regard to the known methods and devices for transfer of jaw models to an articulator, that the methods and devices known from the state of the art—particularly due to the need to record the skull geometry by means of a facial arc and to transfer it to the articulator—are extremely complicated, on the one hand, and are subject to error, on the other hand.

Even passing on the complete facial arc—or at least a bite fork with upper jaw teeth impression and a sensitive coupling mechanism disposed on the bite fork, adjusted to the jaw geometry of the patient—which is absolutely necessary for the purpose of geometry transfer in the state of the art, to the dental technology laboratory is complicated and tends to be expensive because of the need to keep these components on hand in multiple numbers for different patients. Last but not least, there is the additional risk in connection with passing the facial arc or the adjusted coupling mechanism on to the dental technology laboratory, particularly when shipping it, that the precise adjustment that has been made is unintentionally changed as the result of the effect of external forces, and this unavoidably leads to the result of expensive scrap in the dental technology laboratory.

SUMMARY OF THE INVENTION

Against this background, it is the task of the present invention to create a method and a registration system for transfer of jaw models in relation to a hinge axis, with a related bite carrier, as well as furthermore a connection device for setting up a connection for coupling a lower jaw adaptor with a measurement carrier. In this way, the aforementioned disadvantages that exist in the state of the art are supposed to be eliminated.

In particular, the process of the geometry transfer from the patient's head to the articulator is supposed to be decisively improved qualitatively, and in this connection, it is supposed to be significantly simplified at the same time. The method and the device are furthermore supposed to be usable with significantly reduced effort, and with permanent reduction or elimination of error sources, with simultaneously increased flexibility, as compared with the state of the art. Finally, significant simplification of the recording and transfer of jaw geometries and/or models of patients to the articulator, from the aspect of craftsmanship, is also aimed at, so that the corresponding devices and methods can also be used more simply and reliably by an expanded group of persons than is the case for the methods known from the state of the art.

This task is accomplished by means of a method as described herein, and by a registration system as described herein, respectively, particularly using a connection device and a bite carrier, respectively, as described herein.

Preferred embodiments are further described herein.

The method according to the invention serves for the transfer of a jaw model of a patient, in relation to a hinge axis, to an articulator assembly stand with an articulator hinge axis. The articulator assembly stand, which can also be a suitable dental technology articulator, serves, in this connection, for spatially patient-analogous assembly of the jaw model relative to the articulator hinge axis.

In the method according to the invention, first of all a lower jaw adapter is used for transfer of the jaw model; this can be an impression tray, an occlusal bite fork, a para-occlusal registration aid, or a combination of these, for example. In each case, the lower jaw adapter has a suitable bite carrier, whereby the bite carrier can be connected with the lower jaw, i.e. with the lower jaw row of teeth, using an impression mass—with the production of a bite key, in other words an impression of the lower jaw, i.e. the lower jaw row of teeth.

The lower jaw adapter furthermore comprises a coupling device connected with the bite carrier, whereby furthermore, the articulator or assembly stand has a coupling accommodation that is complementary in shape with the coupling device of the lower jaw adapter and can be connected, with shape fit, with the coupling device of the lower jaw adapter, in spatially defined manner. In this connection, the coupling device of the assembly stand is disposed on the assembly stand in reproducibly adjustable manner, relative to the hinge axis of the assembly stand.

Within the scope of the method according to the invention, in a first method step a), impression mass is first disposed on a lower-jaw-side tooth contact surface of the lower jaw adapter.

In a further method step b), connection of the lower jaw adapter with the dental arc of the patient's lower jaw then takes place, by means of the impression mass disposed on the lower jaw adapter. In this connection, an impression of the lower jaw row of teeth is produced in the impression mass disposed on the lower jaw adapter.

Then, in a further method step c), jaw joint registration with hinge axis determination takes place. In this connection, the spatial location of the hinge axis of the patient relative to the lower jaw adapter, particularly relative to the coupling device of the lower jaw adapter, is determined.

The lower jaw adapter is then removed from the jaw, i.e. from the patient's row of teeth, and in a further method step d), the bite carrier is connected with a lower jaw model of the patient, using the impression of the lower jaw row of teeth of the patient in the impression mass on the bite carrier.

Within the scope of a further method step e), the bite carrier and the lower jaw model disposed in the impression of the bite carrier are then disposed in the assembly stand. Placement of bite carrier and lower jaw model in the assembly stand takes place, in this connection, by means of connecting the bite carrier coupling device with the coupling accommodation on the assembly stand that is complementary in shape to the coupling device of the bite carrier.

In other words, this means that bite carrier and lower jaw model experience a preliminary spatially defined fixation relative to the hinge axis of the assembly stand, i.e. relative to a lower jaw assembly plate of the assembly stand connected with the hinge axis, if applicable. In this connection, the coupling accommodation on the assembly stand as well as the lower jaw model connected with it using the bite carrier are at first still in a neutral location relative to the hinge axis of the assembly stand; the position of the hinge axis of the assembly stand relative to the lower jaw model therefore does not yet agree with the actual hinge axis location of the patient relative to the model. However, the precise spatial relationship of the coupling device of the bite carrier—and thus also the spatial relationship of the coupling accommodation of the assembly stand connected with the coupling device—relative to the actual patient hinge axis is already known, on the basis of the previous hinge axis determination.

Against this background, matching of the spatial relative position between the assembly stand coupling accommodation and the hinge axis of the assembly stand to the spatial relative position between the patient hinge axis and the coupling device of the lower jaw adapter determined during the registration, until equality of coverage between patient hinge axis and assembly stand hinge axis relative to the lower jaw model is reached, also takes place in method step e).

In other words, this means that the spatial position of the coupling accommodation of the assembly stand as well as of the bite carrier disposed on the coupling accommodation, with shape fit—together with the lower jaw model disposed on the bite carrier, in defined manner—relative to the hinge axis of the assembly stand, is precisely adjusted in method step e), on the basis of the hinge axis location determined in method step c), in such a manner that the coupling accommodation of the assembly stand is situated spatially, relative to the hinge axis of the assembly stand, in precisely the same relative relationship as the coupling device of the bite carrier relative to the hinge axis of the patient.

This can be done—only as an example—in that the coupling accommodation of the assembly stand, and thus also the bite carrier with the lower jaw model disposed in it, and the hinge articulation points of the assembly stand are displaced, relative to one another, until the spatial relative position between the coupling accommodation of the assembly stand and the assembly stand hinge axis defined by the hinge articulation points precisely cover the previously determined spatial relative position between the coupling device of the bite carrier and the patient hinge axis. In this way, after the method step e) has been carried out, precise agreement of the coordinate system in the assembly stand with the coordinate system of the patient's lower jaw has been achieved, insofar as the relative position between lower jaw and patient hinge axis is concerned.

The invention is furthermore also implemented if the sequence of the method of procedure described in method step e) is interchanged, if, in other words, matching of the spatial relative position of the assembly stand coupling accommodation relative to the coupling stand hinge axis to the spatial relative position between patient hinge axis and lower jaw adapter coupling device takes place first, and only subsequent to this, bite carrier and lower jaw model are disposed in the assembly stand by means of connecting the lower jaw adapter coupling device and the assembly stand coupling accommodation.

Finally, in a further method step f), fixation of the lower jaw model on a lower jaw assembly plate, i.e. on the lower part of the assembly stand or of the articulator, takes place, for example by means of connecting the lower jaw model with the assembly plate using a plaster assembly mass that can harden.

Subsequent to this, positioning of an upper jaw model of the patient, relative to the lower jaw model disposed and positioned in the assembly stand or articulator, can take place—for example using a centered registration taken from the patient in the occlusion position—along with fixation of the upper jaw model on a related upper jaw assembly plate, i.e. on an upper part of the assembly stand or articulator.

The method according to the invention therefore first of all demonstrates the decisive advantage that localization of the hinge axis of the patient is only required relative to the lower jaw—particularly relative to the coupling device of the lower jaw adapter. Since the coupling device of the lower jaw adapter or bite carrier and the coupling accommodation of the assembly stand are configured to be complementary in shape to one another there, and thus can be brought to make contact with one another in reproducibly spatially defined manner, the spatial location of the hinge axis of the patient is therefore also known relative to the coupling accommodation of an assembly stand or articulator, as soon as the coupling device of the bite carrier is connected with the coupling accommodation of the assembly stand or articulator.

The spatial relative relationship between the lower jaw adapter—particularly between the coupling device of the bite carrier of the lower jaw adapter—and the patient hinge axis that is present in the patient and was determined in method step c), is therefore transferred to the assembly stand, i.e. articulator, according to the invention, merely by placing the bite carrier in the assembly stand by means of the coupling device, and by matching the spatial relative position of the assembly stand coupling device and the assembly stand hinge axis with the previously determined patient hinge axis relative to the bite carrier coupling device. This can now be done, thanks to the invention, at practically any desired precision, and, at the same time, in a simple, reproducible manner that was never achieved until now.

At the same time, the complicated and, at the same time, error-prone geometry transfer by means of an arbitrary facial arc (with average axis localization) or by means of a terminal facial arc (with kinematic axis determination) which was always necessary up to now and in the state of the art, is completely eliminated.

In other words, the invention is primarily based on the pioneering recognition that a transfer of the geometric conditions at the skull, particularly at the jaw of the patient, can take place, with decisive advantage and with complete circumvention of the mostly imprecise and furthermore complicated transfer of the skull geometry by means of a facial arc, in that in place of the skull-related transfer, the spatial relative relationship between the lower jaw row of teeth and the patient hinge axis is determined directly, and used for the geometry transfer. This is all the more true since the hinge axis, on the basis of the anatomical conditions of the jaw joint, with its condyles disposed on the lower jaw, is precisely assigned geometrically exclusively to the lower jaw, while the hinge axis relative to the upper jaw can change to a significant degree as a function of the position of the lower jaw. For this reason alone, the transfer of the hinge axis location used throughout the state of the art is already inevitably error-prone, in contrast to the method according to the invention, because of the attempt to record this location on the skull, rather than on the lower jaw, as in the case of the invention.

In this connection, the invention is first of all implemented independent of the manner in which the hinge axis determination takes place in method step c). Thus, the hinge axis determination in method step c) can take place, for example, using various mechanical or electronic methods for kinematic axis determination known from the state of the art, as such. The deciding factor is only that the determination of the spatial location of the patient hinge axis must take place only relative to the lower jaw, particularly only relative to the coupling device of the bite carrier.

According to particularly preferred embodiments of the method according to the invention, however, determination of the hinge axis in method step c) takes place by means of contact-free measurement of an opening movement of the lower jaw, i.e. using contact-free measurement of a relative movement between lower jaw and skull of the patient. This contact-free measurement is advantageous in that in this manner, a practically force-free and therefore undistorted measurement can take place, in which furthermore any feedback effects on the natural jaw movement of the patient are as good as excluded.

The hinge axis determination by means of measuring a relative movement between lower jaw and skull is particularly advantageous in that any inherent head movements of the patient can be recorded and eliminated by means of measurement technology in this manner; the patient's head therefore does not have to be strapped in or otherwise immovably fixed in place, and this is very advantageous for the patient's comfort and thus the patient's willingness to cooperate.

According to another particularly preferred embodiment of the method according to the invention, the hinge axis determination in method step c) also comprises the determination of a skull-related reference plane and a related reference angle relative to the skull-related reference plane, which angle is determined by the spatial position of the lower jaw. In this embodiment, matching of coupling accommodation, bite carrier, and lower jaw model to the reference angle determined during registration, in method step c), takes place in method step e)—by means of corresponding adjustment of the reference angle position of the assembly stand coupling accommodation, which is structured to be adjustable, for this purpose, and thus also adjustment of the bite carrier disposed on the coupling accommodation, with regard to a reference plane of the assembly stand.

With this embodiment, as a result of the precise transfer also of the skull reference plane and the patient-specific reference angle to the assembly stand or articulator that is made possible by this, in particular, full articulation, including the entire jaw joint geometry, also with reference to the reference plane, such as condyle path incline, Bennett angle, retrusion/surtrusion and/or immediate side shift, for example, can also take place.

The contact-free hinge axis determination takes place, according to another, also preferred embodiment of the method according to the invention, in that for contact-free measurement, a measurement carrier is connected with the lower jaw adapter, whereby the measurement carrier has marker elements for contact-free position determination. This embodiment possesses the advantage that the contact-free hinge axis determination can take place by means of reflectors or markers disposed on the measurement carrier, particularly by means of optical image recognition and subsequent digital image processing.

Against this background, it is provided, according to another preferred embodiment of the method according to the invention, that the connection of the measurement carrier with the lower jaw adapter takes place by means of a coupling accommodation disposed on the measurement carrier. In this connection, the coupling accommodation of the measurement carrier is configured to be complementary in shape to the coupling device of the lower jaw adapter (in other words, in turn corresponding in shape to the coupling accommodation of the assembly stand), and furthermore, the spatial position of the marker elements of the measurement carrier relative to the coupling accommodation of the measurement carrier is known.

In this manner, a simple, modular system for connecting and separating also the lower jaw adapter and measurement carrier, for the purpose of contact-free, i.e. optical registration, is obtained. Since the spatial position of the marker elements relative to the coupling accommodation of the measurement carrier is known, and since the spatial position of the marker elements relative to the patient hinge axis is determined during the contact-free or optical measurement, after the measurement, the hinge axis location also relative to the coupling accommodation of the measurement carrier, and with it, in turn, to the coupling device of the bite carrier on the lower jaw adapter is known, since the coupling device of the lower jaw adapter is connected with the coupling accommodation of the measurement carrier during the measurement.

On the basis of the patient hinge axis location that has thus been determined in contact-free manner, relative to the coupling device of the bite carrier on the lower jaw adapter, the hinge axis location in space, again relative to the coupling accommodation, can be reconstructed at any time, with a given spatial position of a coupling accommodation, by means of placing the bite carrier into the coupling accommodation. This is particularly true for the situation in the assembly stand or articulator. If a coupling accommodation is disposed on an assembly stand or articulator, the bite carrier with the tooth impressions, in other words with the bite key, can be connected with this coupling accommodation of the assembly stand or articulator.

If the related jaw model in the tooth impressions of the bite key is disposed on the bite carrier, then the assembly stand joint axis merely has to be brought into the relative position with regard to the coupling device of the bite carrier that was determined during the measurement; this relative position agrees with the coupling accommodation of the assembly stand when the bite carrier is mounted in the assembly stand.

Thus, in the end result—merely by means of passing on the bite carrier with the bite key, and together with the related data concerning the hinge axis location determined on the patient, for example to the laboratory—it is possible to restore the precise spatial relative position between patient lower jaw and patient hinge axis even in the assembly stand or articulator, in the simplest, precise, and reproducible manner.

Preferably, in this connection, the contact-free determination of the patient hinge axis takes place by means of optical image follow-up of the marker elements by means of at least one image-recording camera. This particularly has the advantage that multiple marker elements can be detected and followed by one and the same camera; furthermore, the measurement can take place from a certain distance, with suitable optics and camera resolution, and in this way, it is possible to avoid measurement apparatuses in the immediate vicinity of the patient's head, which might be irritating to the patient.

Against the background of contact-free or optical measurement, it is provided, according to another preferred embodiment of the method according to the invention, that the contact-free measurement includes digital image processing of the images of the marker elements recorded by the camera. In this connection, the digital image processing comprises at least a refocusing operation, for example a Hough transformation. Using the digital image processing with refocusing operation, it is possible to increase the precision of the position determination of the marker elements recorded by the camera to almost any desired degree, particularly if in addition, markers having a structured form, for example comprising multiple concentric circles and/or radial contrast structures are used, since in this way, the informational content of the images of the marker elements produced by the image-recording camera can be multiplied many times.

Furthermore, if the markers are suitably structured graphically or geometrically, there is the additional possibility of determining the three-dimensional spatial position of the markers relative to the image-recording camera, including the distance, the angle, the tilt, the rotation, etc. of the markers relative to the location of the image-recording camera. In this manner, in particular, completely automated calibration of the camera relative to the markers in three-dimensional space can also take place, cf. also the non-published patent application 10 2006 004 197.6, to which reference is hereby explicitly made, and which is incorporated into the disclosure of the present invention, with regard to the graphical design, optical detection, follow-up and spatial localization of marker elements, as well as with regard to automatic calibration of a camera measurement system.

This also leads to the further decisive advantage that it is not necessary to anchor or strap any kind of measurement apparatuses—aside from an extremely light measurement arc on the lower jaw—to the patient's head, which could irritate the patient and thus distort the measurement result, i.e. could make the patient's cooperation in the hinge axis measurement process more difficult, in order to precisely determine the relative movement of the lower jaw and the patient hinge axis location derived from this.

In this connection, the invention can first of all be implemented independent of how the measurement carrier is geometrically structured or designed. For example, it is possible theoretically and in terms of design to configure the measurement carrier in relatively compact manner, to dispose it merely in the immediate vicinity of the coupling device of the lower jaw adapter, and to determine the positions of the marker elements disposed on the measurement carrier, essentially perjorially, by means of optical follow-up using one or more cameras.

According to a particularly preferred embodiment of the method according to the invention, however, the measurement carrier is configured as a lower jaw measurement arc, whereby the marker elements for contact-free position determination are disposed on the measurement arc, close to the jaw joint.

In this manner, on the one hand, a highly precise hinge axis determination can take place by means of multiple markers disposed on both sides of the jaw joint, in each instance, for example, on the lower jaw measurement arc, at a relatively great distance—and thus with a precise measurement base. On the other hand, with this placement of the measurement arc markers close to the jaw joint, possible additional reference markers for determining the reference plane and/or for detecting and eliminating, by means of measurement technology, skull movements of the patient, can also be disposed on the patient's skull, close to the jaw joint, and thus detection of both the measurement arc markers and of the reference markers can take place with one and the same sensor device or camera, in each instance.

This means, in other words, that a complete spatial determination of the position and location of the measurement arc (and thus also of the patient hinge axis), furthermore simultaneous determination of the skull-related reference plane and of the reference angle, as well as furthermore elimination of skull movements by the patient, by means of measurement technology, can take place using merely two image-recording cameras that are already directed at the region of the two jaw joints.

In order to implement the method according to the invention, it is first of all not significant in what manner matching of the spatial relative position of the coupling accommodation, if applicable together with bite carrier and lower jaw model, with regard to the hinge axis of the assembly stand, takes place in the assembly stand or articulator in method step e), as long as it is assured that after matching, the spatial relative relationship between the coupling accommodation of the assembly stand and the assembly stand hinge axis agrees with the spatial relative relationship between the coupling device of the lower jaw adapter and the patient hinge axis that was determined on the patient previously.

In particular, matching of the spatial relative position between coupling accommodation and assembly stand hinge axis to the corresponding, measured spatial relative position between lower jaw adapter coupling device and patient hinge axis, in the assembly stand, can take place using manual mechanical adjustment either of the coupling accommodation or of the assembly stand hinge axis, for example. For this purpose, the assembly stand can be set up in such a manner, for example, that the two joint sockets can be adjusted, by means of corresponding parallel guides disposed on the assembly stand, which guides can be adjusted and fixed in place, in all three spatial directions, until agreement is reached between the assembly stand hinge axis and the patient hinge axis, relative to the coupling accommodation on the assembly stand.

According to a preferred embodiment of the method according to the invention, however, it is provided that in method step e), matching of the spatial relative position of the coupling accommodation, if applicable together with the bite carrier and lower jaw model already disposed on the coupling accommodation, takes place in the assembly stand, with regard to the hinge axis of the assembly stand, by means of electro-mechanical actuators disposed on the assembly stand, for example by means of servomotors.

In terms of design, this can be implemented, for example—but by no means exclusively—in that a servomotor adjustment of the two hinge joint points, i.e. joint sockets of the assembly stand that define the assembly stand hinge axis takes place until agreement is reached between the assembly stand hinge axis and the patient hinge axis, relative to the coupling accommodation on the assembly stand.

This embodiment offers particularly great reliability and particularly great ease of operation for the user, because of the extensive automation of the adjustments of the assembly stand that can be achieved with this. This is particularly true if the displacement of the assembly stand hinge axis relative to the assembly stand coupling accommodation takes place automatically, on the basis of data recorded during registration and passed on to the dental technology laboratory, for example, concerning the spatial location of the hinge axis of the patient relative to the coupling device of the lower jaw adapter.

According to another embodiment of the method according to the invention, as an alternative to the mechanization of the assembly stand, for example with servomotors, it is provided that the placement of bite carrier and lower jaw model into the assembly stand as well as the matching of the spatial relative position of the assembly stand coupling accommodation and the bite carrier and lower jaw model disposed in it, takes place in method step e) using a lower jaw transfer arc. In this connection, the lower jaw transfer arc comprises two axis marking elements, for example two axis marking tips, as well as a coupling accommodation for the coupling device of the bite carrier, which simultaneously forms the assembly stand coupling accommodation, whereby the spatial relative position between the connecting straight lines of the axis marking elements and the coupling device of the lower jaw transfer arc is adjustable on the lower jaw transfer arc, and can be fixed in place in agreement with the patient hinge axis location determined in method step c), relative to the coupling device of, the bite carrier.

In this connection, according to this embodiment, placement of bite carrier and lower jaw model in the assembly stand as well as matching of the spatial relative position of the assembly stand coupling accommodation relative to the assembly stand hinge axis takes place in method step e), using the lower jaw transfer arc, in such a manner that the axis marking elements of the lower jaw transfer arc are connected with axis accommodation points of the assembly stand disposed on the hinge axis of the assembly stand, i.e. brought into coverage with these axis accommodation points.

This means, in other words, that according to this embodiment of the method according to the invention, the spatial relative relationship between the patient hinge axis and the coupling device of the bite carrier is mechanically coded on the lower jaw transfer arc in the form of the relative position between the axis marking tips of the lower jaw transfer arc and the coupling device of the lower jaw transfer arc, which position is adjusted and fixed in place on the lower jaw transfer arc. In this connection, this coding of the lower jaw transfer arc preferably takes place immediately after the hinge axis determination, for example by means of displacement of the marking tips of the lower jaw transfer arc, until coverage equality of the marking tips on the lower jaw transfer arc with the patient hinge axis that was determined. In this connection, transfer of the patient-specific reference angle determined on the patient, with regard to a skull reference plane, to the assembly stand can take place at the same time, in that an angle setting element is provided in the region of the marking tips of the lower jaw transfer arc, which element can be used to check or adjust the reference angle position of the lower jaw transfer arc on the assembly stand.

Against this background, it is provided, according to another preferred embodiment of the method according to the invention, that the lower jaw measurement arc forms the lower jaw transfer arc, at the same time. Thus, the mechanical transfer of the patient hinge axis location to the assembly stand or articulator can be carried out without replacing the lower jaw arc, using the same lower jaw arc with which the hinge axis determination itself was carried out.

According to another embodiment of the method according to the invention, it is provided that the coupling device of the lower jaw adapter is adjustably disposed on the lower jaw adapter, relative to the tooth contact surfaces of the lower jaw adapter, preferably by means of a ball joint.

This embodiment has the background that in the case of the method according to the invention in its most general form, the relative relationship between the patient hinge axis and the coupling device of the lower jaw adapter is transferred to the assembly stand. For this purpose, is it advantageous if the coupling device of the lower jaw adapter can be brought close to the standard position of the coupling device, with reference to the hinge axis zero position of the assembly stand, already on the patient, relative to the tooth contact surfaces of the lower jaw adapter, in such a manner that later, on the assembly stand, only slight adjustments have to be made in order to bring the assembly stand hinge axis into coverage with the patient hinge axis.

Furthermore, in this manner, simple adaptation of the lower jaw adapter to different jaw and skull geometries of different patients can take place. This is particularly important if a standardized lower jaw measurement arc and/or a para-occlusal registration aid is used to determine the hinge axis, since in this case, there would be hardly any other possibilities—in other words without an adjustable coupling device—for varying the position of the lower jaw measurement arc relative to the dental arc of the lower jaw, i.e. relative to the lower jaw of the patient, and thus for approximately adjusting the lower jaw measurement arc before the measurement.

According to another embodiment of the method according to the invention, the bite carrier of the lower jaw adapter is configured as an occlusal bite fork. In this embodiment, in particular, a ball joint or another adjustable connection between the coupling device of the lower jaw adapter and the tooth contact surface of the lower jaw adapter can be eliminated. This is because an occlusal bite fork generally offers sufficient freedom of movement for an approximate adjustment, in such a manner that the lower jaw measurement arc is situated approximately in the correct measurement position relative to the jaw of the patient, in advance of the hinge axis determination. In the case of exclusive use of an occlusal bite fork, this embodiment of the method according to the invention is particularly suited for a simple, robust, and cost-advantageous registration and/or hinge axis determination, with subsequent geometry transfer to the assembly stand.

Against this background, it is provided, according to another embodiment of the method according to the invention, that in an additional method step c'), impression mass is additionally disposed on the upper-jaw-side tooth contact surface of the bite carrier configured as an occlusal bite fork. Subsequently, in a further method step c"), production of an impression of the upper jaw dental arc in the impression mass disposed on the upper-jaw-side tooth contact surface of the bite carrier takes place.

This means, in other words, that the relative position of upper jaw and lower jaw—using the impressions of both dental arcs—is coded on the occlusal bite carrier. Thus, both the lower jaw model and the upper jaw model of the patient can be disposed and fixed in place in the assembly stand or articulator, in the precisely correct position and location—simply on the basis of handing the bite carrier, together with the data concerning the patient hinge axis location, to the dental technician, for example.

According to another embodiment—an alternative embodiment to the one described above—of the method according to the invention, the bite carrier of the lower jaw adapter is configured as a para-occlusal registration aid. In this manner, the jaw joint registration can take place with particularly great precision, since when using a para-occlusal registration aid, no kind of interference and no kind of unnatural occlusal distance are induced.

According to another preferred embodiment of the method according to the invention, it is provided that the lower jaw adapter comprises an occlusal bite fork with a coupling device as a bite carrier, as well as furthermore a para-occlusal registration aid with an intermediate adapter. In this connection, the intermediate adapter has a coupling accommodation for the coupling device of the occlusal bite fork. According to this embodiment, first of all the para-occlusal registration aid with the intermediate adapter is used in method step c) for the hinge axis determination, and in this connection, the spatial location of the patient hinge axis relative to the coupling accommodation of the intermediate adapter is determined.

According to this embodiment, the method has the additional method steps $c_1$) and $c_2$) which are presented below. In a first additional method step $c_1$), after the hinge axis determination, the occlusal bite fork is connected, by means of the intermediate adapter, with the para-occlusal registration aid that is still disposed on the lower jaw row of teeth of the patient. In this connection, another impression of the lower jaw dental arc of the patient is produced, in an impression mass disposed on the tooth contact surface of the occlusal bite fork.

In other words, this means that in this way, in method step $c_1$), the spatial relative position between the patient hinge axis and the coupling accommodation of the intermediate adapter previously determined in method step c), by means of placing the occlusal bite fork on the coupling accommodation of the intermediate adapter, is now also assigned to the coupling device of the occlusal bite fork, whereby at the same time, the spatial relative position also of the lower jaw dental arc of the patient, relative to the coupling accommodation of the intermediate adapter and thus also to the coupling device of the occlusal bite fork, is coded onto the occlusal bite fork.

Thus, in the end result, the occlusal bite fork again represents the bite carrier in this case, as well, on which precisely the spatial relative position between patient hinge axis and coupling accommodation of the intermediate adapter is coded, i.e. stored, as a data carrier, on the basis of the tooth impressions as a bite key.

Subsequently, in a further method step $c_2$), separation of the occlusal bite fork from the para-occlusal registration aid takes place, along with removal of the occlusal bite fork and the para-occlusal registration aid from the lower jaw of the patient.

Thus, in this embodiment of the method according to the invention, after the method steps $c_1$) and $c_2$), the spatial relative relationship between patient hinge axis, lower jaw dental arc, and coupling device is again coded only on the occlusal bite fork—together with the related hinge axis data set.

Accordingly, in this case, as well, the transfer of jaw model and jaw geometry to the assembly stand can take place merely by passing on the occlusal bite fork as the bite carrier, together with the hinge axis data set, although according to this embodiment of the method according to the invention, the actual registration or hinge axis determination took place not with the occlusal bite fork, but rather in particularly precise and disruption-free manner, with the para-occlusal registration aid.

Against this background, it is provided according to another, particularly preferred embodiment of the method according to the invention, that the intermediate adapter of the para-occlusal registration aid is connected with the para-occlusal registration aid in adjustable manner, for example by means of a ball joint, relative to the tooth contact surfaces of the para-occlusal registration aid. This also serves to undertake an approximate adjustment of the coupling accommodation disposed on the intermediate adapter, in advance of the jaw joint registration or hinge axis determination, so that later, on the assembly stand, only slight adjustments have to be made, in order to bring the assembly stand coordinate system into agreement with the lower jaw coordinate system of the patient.

Furthermore, in this manner, simple adaptation of the lower jaw adapter also to different jaw and skull geometries of different patients can take place in advance of the hinge axis determination, and this is particularly important if a standardized, rigid lower jaw measurement arc is used for the hinge axis determination on the patient.

According to another, also preferred embodiment of the method according to the invention, it is provided, in this connection, that the intermediate adapter can be separated from the para-occlusal registration aid. For this purpose, the intermediate adapter comprises a connection accommodation, and the para-occlusal registration aid comprises a connection device that is complementary in shape to the connection accommodation.

In this connection, preferably at least two intermediate adapters are present, which can be replaced with one another and correspond to one another in dimensions and shape, with regard to connection accommodation and coupling accommodation, whereby the first intermediate adapter simultaneously forms the measurement carrier, for example the lower jaw measurement arc, or is connected with it, with which the contact-free hinge axis determination takes place, for example. Another intermediate adapter that is present, on the other hand, essentially represents merely a coupling accommodation for the occlusal bite fork, as well as a connection accommodation for the para-occlusal registration aid, for use in method step $c_1$).

This means, in other words, that the hinge axis determination according to this embodiment of the method according to the invention can take place by means of the para-occlusal registration aid, in such a manner that the para-occlusal registration aid is disposed on the connection accommodation of the first intermediate adapter, which is configured as a lower jaw measurement arc, for example, after which the hinge axis determination or jaw joint registration takes place. Subsequent to this, the first intermediate adapter, configured as a lower jaw measurement arc, can be removed from the para-occlusal registration aid, and instead, the second intermediate adapter can be connected with the para-occlusal registration aid by means of its connection accommodation.

Now, again—as above in method step $c_1$)—the coupling device of the occlusal bite fork can be disposed on the coupling accommodation of the—in this case second—intermediate adapter, and the bite key can be taken off the lower jaw row of teeth by means of the occlusal bite fork as the bite carrier, and coded on the occlusal bite fork. This means, in particular, that the transfer or coding of the bite key from the para-occlusal registration aid to the occlusal bite fork that takes place in method step $c_1$) can be carried out without the lower jaw measurement arc that might cause problems, but— by means of the second intermediate adapter—at an unchanged great precision.

According to a particularly preferred embodiment of the method according to the invention, in this connection, coupling of the connection device of the para-occlusal registration aid with the connection accommodation of the intermediate adapter takes place by means of the attraction force of a coupling magnet disposed on the connection device or on the connection accommodation, in a magnetic connection region.

This embodiment particularly possesses the advantage that in this manner, extensively automatic engagement of the connection device of the para-occlusal registration aid and of the connection accommodation of the intermediate adapter into one another can take place. In this connection, this engagement can take place to the greatest possible extent without any additional effect of force, particularly without any effect of force supported externally, which would otherwise represent a possible error source, due to the risk of bringing the ball joint disposed on the para-occlusal registration aid, for example, out of adjustment, as a result.

Thanks to the magnetically initiated fixation, the action and reaction forces required for engagement of connection device and connection accommodation therefore precisely cancel one another out, and great precision of the connection between para-occlusal registration aid and intermediate adapter, i.e. lower jaw measurement arc, is guaranteed.

Separation of the magnetic coupling between the connection device of the para-occlusal registration aid and the connection accommodation of the intermediate adapter takes place, in this connection, preferably in that the coupling magnet is moved out of the connection region at an angle relative to the main magnetic force direction—preferably in a perpendicular direction relative to the main magnetic force direction.

This is particularly advantageous in that in this manner, the coupling magnet can be moved out of the connection region between connection device and connection accommodation slowly and uniformly, with only a minimal activation force. Thus, in this manner, the magnetic connection can be released carefully and yet in simple manner—again with the lowest possible external effect of force—without error-inducing reaction forces occurring because of the separation process between para-occlusal registration aid and intermediate adapter, which could impair the precision of the positioning of the para-occlusal registration aid relative to the lower jaw dental arc.

According to another preferred embodiment of the method according to the invention, it is provided that the bite carrier comprises a data memory for storing registration data, or that a data memory device for storing registration data can be disposed on the bite carrier. This makes it possible that after the jaw joint registration or hinge axis determination on the patient has been carried out, some or all of the registration data can be stored in the data memory of the bite carrier. Subsequently, solely and alone the bite carrier, with the tooth impressions disposed on it, as the bite key, as well as the data contained in the data memory device, particularly concerning the patient hinge axis location, must be passed on to the dental technology laboratory, for example.

In this manner, not only the data concerning the patient hinge axis location, but instead, particularly all the data relating to the complete jaw geometry of the patient, can furthermore be stored in the data memory of the bite carrier. The bite carrier with the dental arc impression(s) can therefore, in itself, and without any other aids or documents, form the complete and perfect documentation of the entire patient jaw geometry and all relevant gnathological relationships of the patient. This is not only of inestimable advantage for the transfer of jaw geometries to the dental technology laboratory, for example, but furthermore also opens up decisive new fields of use and simplifications, for example but by no means exclusively also in forensics.

Thus, the dental technician is able, solely on the basis of the bite carrier received, with the data memory device disposed in it, to place jaw models of the patient into the assembly stand or into the articulator, in the correct position and location, and to make plaster models. In this way, transferring and passing on the data concerning the geometry of the patient's jaw joint, including the precise hinge axis location, for example to the dental technician laboratory, can be simplified and accelerated in almost revolutionary manner as compared with the state of the art, whereby at the same time, the error sources present in the state of the art can be reduced or eliminated, and furthermore, significant costs can be saved.

Against this background, it is even possible to present an assembly stand or articulator that adjusts itself, fully automatically, to the precise jaw joint geometry of a patient. Aside from the coupling accommodation for the bite carrier and aside from the adjustment of the relative position between coupling accommodation and hinge axis, for example by means of servomotors, such an assembly stand or articulator requires, in addition, only an interface by way of which the data contained in the data memory device of the bite carrier concerning the jaw joint geometry and patient hinge axis location can be read out and converted to corresponding control commands for the servomotors of the articulator or assembly stand.

In the dental technology laboratory, in this case, all that has to be done is to insert the bite fork that has been received, with the geometry data of the patient stored in it, into the coupling accommodation of the assembly stand or articulator, and afterwards, the assembly stand or articulator takes on and reproduces the jaw joint geometry of the patient, in fully automatic and precise manner.

According to another particularly preferred embodiment of the method according to the invention, the spatial position of the hinge axis of the patient is determined, in method step c), both in a habitual intercuspidation position and in a therapeutic relative position between upper jaw and lower jaw that differs from the habitual position. In this connection, the therapeutic relative position can be established, for example, on the basis of electronic recording and assessment preferably of the entire movement space of the jaw joint of the patient.

The method according to this embodiment first of all comprises, for one thing, the additional method step g), in which—for example by means of a centered registration—the positioning of an upper jaw model of the patient relative to the lower jaw model takes place in the assembly stand, as does the fixation—for example by means of plastering it on—of the upper jaw model to an upper jaw assembly plate of the assembly stand. In this way, first of all the spatial location of the two jaws of the patient, as well as the related hinge axis location, is precisely reproduced in the assembly stand or articulator, in the selected habitual position.

Subsequently, in a further method step h), a relative displacement of the upper jaw assembly plate together with the upper jaw model with regard to the lower jaw assembly plate together with the lower jaw model takes place, until the desired therapeutic relative position between the rows of teeth of the upper jaw and of the lower jaw is reached.

In other words, this embodiment of the method according to the invention first of all comprises that the jaw models of the patient are attached in the assembly stand or articulator in a habitual position determined for the patient, for example plastered in. Subsequently, adjustment takes place, i.e. moving to the therapeutic relative position between upper jaw and lower jaw that was previously determined or established. The latter can take place with either computer control or visual monitor control, and for this purpose, a suitable sensor system, for example cameras and markers, are disposed on the assembly stand or articulator.

However, setting of the therapeutic position in the assembly stand or articulator can also take place—as is provided according to another embodiment of the method according to the invention—by means of directly moving to the therapeutic relative position previously established for the patient, for example by means of an articulator or assembly stand that can be adjusted by means of servomotors. In this case, it is not necessary that once again, a registration device specifically has to be disposed on the assembly stand or articulator, for the purpose of visual control when moving to the therapeutic relative position.

Thanks to these embodiments of the method according to the invention, the therapeutic relative positions of upper jaw and lower jaw that are important in many cases can be precisely and reproducibly produced also in an assembly stand or articulator. In this way, it is made possible that therapeutic registrations, therapeutic bite-down aids, and the like, for example, can already be completed in the laboratory, with the greatest and at the same time reproducible precision. In this way, the scope of the work that still has to be carried out in the patient's mouth itself can be reduced to an absolute minimum or even eliminated, and this can significantly increase acceptance by the patient and, at the same time, lead to a lasting cost reduction.

Another embodiment of the method according to the invention provides that the articulator assembly stand is an essentially conventional articulator or represents its upper part. This means, in other words, that the assembly stand in which the positioning of the lower jaw model of the patient relative to the hinge axis of the assembly stand takes place, on the basis of the data concerning the patient hinge axis location relative to the coupling device of the bite carrier, is essentially identical with an articulator or, at the same time, represents the upper part of the articulator. In this manner, replacement of the assembly stand upper part with a separate articulator upper part, which is otherwise necessary, and, if applicable, separate assembly of articulator joint boxes after the model and geometry transfer to the assembly stand can be eliminated.

This embodiment of the method according to the invention can be implemented, in the simplest case, in that an otherwise essentially conventional articulator is equipped with a coupling accommodation for accommodating the coupling device of a bite key, whereby means for adjustment, precision adjustment, and fixation of the spatial relative position of the articulator hinge axis relative to the articulator coupling accommodation are additionally provided on the articulator.

Thus, the bite carrier can simply be directly attached to the coupling accommodation of the articulator, and the articulator hinge axis—before or afterwards—can be brought into the same spatial relative position with regard to the articulator hinge axis, relative to the articulator coupling device, as it corresponds to the relative position between bite carrier coupling device and patient hinge axis previously determined on the patient.

The invention furthermore relates to a registration system for the transfer of a jaw model and jaw model geometry of a patient in relation to the hinge axis, to an articulator assembly stand or articulator. In this connection, the registration system first of all comprises, in and of itself, and in known manner, a jaw adapter with a bite carrier and a bite key that can be disposed on the bite carrier, in the form of an impression of a row of the patient's teeth. In this connection, the bite carrier of the jaw adapter has a coupling device that can be connected with a coupling accommodation that can be disposed on the assembly stand in a reproducible relative position with regard to the assembly stand hinge axis, in spatially defined manner and with shape fit, whereby the assembly stand coupling accommodation is configured to be complementary in shape to the coupling device of the bite carrier.

However, according to the invention, the registration system is characterized in that the jaw adapter is a lower jaw adapter, and the bite carrier is a lower jaw bite carrier. In this connection, the lower jaw adapter can be connected with a measurement carrier for determining the patient hinge axis relative to the coupling device of the bite carrier, and the spatial position of the coupling accommodation of the assembly stand relative to the hinge axis of the assembly stand is defined and reproducibly adjustable.

Using the registration system according to the invention, first of all precise localization of the hinge axis of the patient relative to the lower jaw, i.e. relative to the coupling device of the bite carrier disposed on the lower jaw row of teeth can take place. In this connection, the determination of the patient hinge axis location takes place by means of the measurement carrier connected with the lower jaw adapter for this purpose, on the basis of the known dimensions and geometry of the measurement carrier, as well as its connection with the lower jaw adapter.

After the hinge axis determination carried out by means of the registration system according to the invention, the precise spatial relative relationship between the patient hinge axis, the lower jaw tooth impression on the bite carrier, and the geometry of the bite carrier—particularly the coupling device of the bite carrier—is thus first of all known. This spatial relative relationship can then easily be transferred into the assembly stand or articulator, thanks to the spatial position of the coupling accommodation of the assembly stand that is adjustable relative to the hinge axis of the assembly stand or articulator, with the greatest precision and with reduction or elimination of error sources, in that the bite carrier is disposed on the coupling accommodation of the assembly stand by means of its coupling device, and that the coupling accommodation of the assembly stand is adjusted relative to the assembly stand hinge axis in accordance with the hinge axis location determined for the patient.

Preferably, in this connection, the measurement carrier has a coupling accommodation that is complementary in shape to the coupling device of the lower jaw adapter. In this manner, a simple and fast modular connection possibility between lower jaw adapter and measurement carrier is obtained. For example, different measurement carriers can be used, depending on the precision requirements, or optionally, electronic/contact-free or mechanical measurement carriers as well as the related measurement methods can be used in connection with the registration system.

According to a preferred embodiment of the invention, the lower jaw bite carrier is configured as an occlusal tray, whereby the occlusal tray comprises an occlusal bite fork for accommodating the tooth impressions, i.e. the bite key of the patient, as well as a cuff that can be releasably connected with the bite fork.

This allows producing the bite key and, if applicable, carrying out a jaw joint registration, in such a manner that bite fork and cuff are first of all connected with one another, for example inserted into one another. In this way, the impression mass, which is still in paste form, is effectively prevented from flowing away to the side when the bite key is produced. After the impression mass has hardened, however, the cuff can be separated from the bite fork. In this manner, the bite key, now disposed on the bite fork in the form of the hardened impression mass, can be easily and freely processed or cut, accessible from all sides.

According to an alternative embodiment of the invention, the lower jaw bite carrier is configured as a para-occlusal registration aid, whereby the coupling device of the bite carrier is connected with the tooth contact surfaces of the bite carrier by means of an articulation device that is preferably configured as a ball joint.

This embodiment has the background that the relative relationship between the patient hinge axis and the coupling device of the lower jaw adapter is supposed to be determined by means of the registration system according to the invention and transferred to the assembly stand. For this purpose, it is advantageous if the coupling device of the lower jaw adapter, relative to the tooth contact surfaces of the lower jaw adapter, can already be brought close to the standard position of the coupling device with regard to the hinge axis zero position of the assembly stand on the patient, in such a manner that later, on the assembly stand, only slight adjustments have to be made in order to bring the assembly stand hinge axis into coverage with the patient hinge axis.

Furthermore, in this manner, simple adaptation of the lower jaw adapter to different jaw and skull geometries of different patients can take place. This is particularly important if a standardized lower jaw measurement arc and/or a para-occlusal registration aid is/are used for the patient hinge axis determination, since in this case otherwise—in other words without an adjustable coupling device—there would be hardly any possibilities for varying the position of the lower jaw measurement arc relative to the dental arc of the lower jaw, i.e. relative to the lower jaw of the patient, and therefore for approximately regulating the lower jaw measurement arc before the measurement.

According to a particularly preferred embodiment of the invention, the measurement carrier is configured as a lower jaw measurement arc with marker elements for contact-free position determination, whereby the marker elements are furthermore disposed close to the jaw joint.

In this manner, on the one hand, the registration system makes a precise patient hinge axis determination possible, by means of multiple markers disposed on both sides of the jaw joint, for example, on the lower jaw measurement arc, at a relatively great distance from one another—thereby forming a highly precise measurement basis. On the other hand, in the case of such a placement of the measurement arc markers close to the jaw joint, any additional reference markers for determining the reference plane and/or for recording and eliminating skull movements of the patient, by means of measurement technology, can also be disposed on the skull of the patient, close to the jaw joint, and thus, recording of both the measurement markers and the reference markers can take place with one and the same measurement device, for example.

This means, in other words, that according to this embodiment of the invention, complete spatial recording of the position and location of the measurement arc (and thus also of the patient hinge axis), furthermore simultaneous recording of the skull-related reference plane and the patient reference angle, and furthermore, elimination of skull movements of the patient, by means of measurement technology, can take place simply using two measurement systems that are already disposed in the region of the two jaw joints, for example image-recording cameras.

Such a preferred embodiment of the invention provides that the assembly stand has electro-mechanical actuators, for example servomotors, for adjusting the coupling accommodation disposed on the assembly stand relative to the connecting straight line of the assembly stand articulation points. In this manner, the hinge axis location determined for the patient can be precisely reproduced on the assembly stand or articulator, mechanized, i.e. automated to the greatest possible extent, for example by means of corresponding displacement of the coupling accommodation or, instead, the joint sockets of the assembly stand, relative to an assembly plate of the assembly stand.

According to another embodiment of the registration system according to the invention, alternative to the servomotor mechanization of the assembly stand, it is provided that the assembly stand coupling accommodation—which serves to accommodate the coupling device of the bite carrier—is formed by a coupling accommodation of a lower jaw transfer arc that can be disposed on the assembly stand in a defined spatial relative position with regard to the hinge axis of the assembly stand. In this connection, the lower jaw transfer arc comprises two axis marking elements, for example axis marking tips, for the purpose of spatially defined placement of the lower jaw transfer arc on the assembly stand.

Furthermore, the lower jaw transfer arc has a coupling accommodation that simultaneously forms the assembly stand coupling accommodation, for the coupling device of the bite carrier, whereby the spatial relative position between the connecting straight line of the axis marking elements and the coupling device of the lower jaw transfer arc is adjustable on the lower jaw transfer arc, can be brought into agreement with the hinge axis location determined for the patient, and can be fixed in place on the lower jaw transfer arc.

In this connection, according to this embodiment, placement of bite carrier and lower jaw model in the assembly stand, as well as precision adjustment of the spatial relative position of the assembly stand coupling accommodation relative to the assembly stand hinge axis takes place purely mechanically, using the lower jaw transfer arc, in such a manner that the axis marking elements of the lower jaw transfer arc are connected with axis accommodation points of the assembly stand disposed on the hinge axis of the assembly stand, i.e. are brought into coverage with these axis accommodation points.

In other words, this means that according to this embodiment of the method according to the invention, the spatial relative relationship between the patient hinge axis and the coupling device of the bite carrier is mechanically coded on the lower jaw transfer arc in the form of the relative position between the axis marking tips of the lower jaw transfer arc and the coupling device of the lower jaw transfer arc, which position is set and fixed in place. In this connection, this coding of the lower jaw transfer arc preferably takes place immediately after the hinge axis determination, for example by means of displacement of the marking tips of the lower jaw transfer arc, until coverage equality of the marking tips on the lower jaw transfer arc with the patient hinge axis that was determined. In this connection, transfer of the patient-specific reference angle determined on the patient, with regard to a skull reference plane, to the assembly stand can take place at the same time, in that an angle setting element is provided in the region of the marking tips of the lower jaw transfer arc, which element can be used to check or adjust the reference angle position of the lower jaw transfer arc on the assembly stand.

Against this background, it is provided, according to another preferred embodiment of the invention, that the lower jaw measurement arc forms the lower jaw transfer arc, at the same time. Thus, the mechanical transfer of the patient hinge axis location to the assembly stand or articulator can be carried out without replacing the lower jaw arc, using the same lower jaw arc with which the hinge axis determination itself was carried out.

According to another, particularly preferred embodiment of the invention, the coupling accommodation disposed on the assembly stand for coupling on the bite carrier is adjustable along a guide device configured in arc shape, relative to an assembly plate of the assembly stand. In this connection, the center point of the arc coincides with the assembly stand hinge axis in its zero position, i.e. in its starting position before transfer of the jaw geometry of the patient to the assembly stand.

This embodiment of the invention allows precise transfer also of the skull reference plane, as well as of the patient-specific reference angle to the assembly stand or articulator. In this way, after the geometry transfer by means of the registration system, in particular, also a full articulation including the jaw joint geometry in relation to the reference plane, such as condyle path incline, Bennett angle, retrusion/surtrusion, and/or immediate side shift, can take place.

Another preferred embodiment of the invention provides that the lower jaw adapter comprises an occlusal bite fork with a coupling device as a bite carrier, as well as a para-occlusal registration aid. In this connection, the para-occlusal registration aid furthermore has an intermediate adapter with a coupling accommodation for the coupling device of the occlusal bite fork. With this embodiment, it is made possible that only the para-occlusal registration aid is used for the patient hinge axis determination, at first, and this allows particularly precise and interference-free determination of the patient hinge axis location, without interference with regard to the occlusion of the patient. Subsequent to the patient hinge axis determination carried out with the para-occlusal registration aid, the bite key as well as the spatial information determined with regard to the patient hinge axis relative to the para-occlusal registration aid can then be transferred to the occlusal bite fork—by means of the intermediate adapter. At the same time, an impression of the row of teeth of the lower jaw is also produced on the occlusal bite fork.

In other words, this means that in the case of this embodiment, the spatial relative position between the patient hinge axis and the para-occlusal registration aid determined within the scope of the patient hinge axis determination is also assigned to the coupling device of the occlusal bite fork—by means of a defined, shape-fit connection between the para-occlusal registration aid and the occlusal bite fork, by means of the intermediate adapter. In this connection, the spatial relative position of the lower jaw dental arc of the patient is thus additionally coded onto the occlusal bite fork.

Accordingly, in this case, as well, the occlusal bite fork again represents the bite carrier, on which precisely the spatial relative position between patient hinge axis and coupling accommodation of the intermediate adapter is coded, i.e. stored, as a data carrier, on the basis of the tooth impression as a bite key.

Preferably, in this connection, the intermediate adapter of the para-occlusal registration aid is disposed on the para-occlusal registration aid in adjustable manner, relative to the tooth contact surfaces of the para-occlusal registration aid, preferably by means of a ball joint.

In this manner, simple adaptation of the para-occlusal registration aid to different jaw and skull geometries of different patients can take place by means of corresponding adjustment of the ball joint. This is particularly important if a standardized lower jaw measurement arc is used for the patient hinge axis determination, since otherwise, without an adjustable coupling device, there would be hardly any possibilities for varying the position of the lower jaw measurement arc relative to the dental arc of the lower jaw, i.e. relative to the lower jaw of the patient, and thus for approximately adjusting the lower jaw measurement arc before the measurement.

Preferably, in this connection, the intermediate adapter can be separated from the para-occlusal registration aid, whereby the intermediate adapter has a connection accommodation, and the para-occlusal registration aid has a connection device that is complementary in shape to the connection accommodation. Particularly preferably, the registration system furthermore has at least two intermediate adapters are present, which can be replaced with one another. In this connection, the first intermediate adapter simultaneously forms the measurement carrier, for example the lower jaw measurement arc for the preferably contact-free hinge axis determination, for example, or is connected with it.

A second intermediate adapter, on the other hand, essentially merely makes available a coupling accommodation for the occlusal bite fork, as well as a connection accommodation for the para-occlusal registration aid.

In other words, this embodiment brings with it that the patient hinge axis determination first of all can take place by means of the para-occlusal registration aid, in such a manner that the para-occlusal registration aid is disposed on the connection accommodation of the first intermediate adapter, which is configured as a lower jaw measurement arc, for example. Afterwards, the first intermediate adapter, configured as a lower jaw measurement arc, can be removed from the para-occlusal registration aid, and instead, the second intermediate adapter can be connected with the para-occlusal registration aid by means of its connection accommodation.

At the same time, again, the coupling device of the occlusal bite fork can be disposed on the coupling accommodation of the second intermediate adapter, and the bite key can be taken off the lower jaw row of teeth by means of the occlusal bite fork as the bite carrier, and coded on the occlusal bite fork.

This means, in particular, that the transfer or coding of the bite key from the para-occlusal registration aid to the occlusal bite fork can be carried out without the lower jaw measurement arc that might cause problems in this connection, but—by means of the second intermediate adapter, which corresponds in shape to the first—at an unchanged great precision.

According to a particularly preferred embodiment of the registration system according to the invention, the connection device of the para-occlusal registration aid, or the connection accommodation of the intermediate adapter, in this connection, comprises a coupling magnet disposed in a magnetic connection region, for coupling the connection device with the connection accommodation.

This embodiment brings the advantage with it that in this manner, extensively automatic engagement of the connection device of the para-occlusal registration aid and of the connection accommodation of the intermediate adapter into one another can take place. In this connection, this engagement can take place practically without any additional effect of force, particularly without any effect of force supported externally, since the latter would represent a possible error source, due to the risk of bringing the ball joint disposed on the para-occlusal registration aid, for example, out of adjustment, as a result.

This is because thanks to the magnetically initiated fixation, the action and reaction forces required for engagement of connection device and connection accommodation precisely cancel one another out, and great precision of the connection between para-occlusal registration aid and intermediate adapter, i.e. lower jaw measurement arc, is thus guaranteed.

For the purpose of separating the magnetic coupling between the connection device of the para-occlusal registration aid and the connection accommodation of the intermediate adapter, it is provided, according to another preferred embodiment of the registration system according to the invention, that the coupling magnet can be moved out of the connection region at an angle relative to the main magnetic force direction, preferably in a perpendicular direction relative to the main magnetic force direction.

This is particularly advantageous in that in this manner, the coupling magnet can be moved out of the connection region between connection device and connection accommodation with a minimal activation force. Thus, in this manner, the magnetic connection can be released in simple manner— again with the lowest possible external effect of force—without error-inducing reaction forces occurring because of the separation process between para-occlusal registration aid and intermediate adapter, which could impair the precision of the positioning of the para-occlusal registration aid relative to the lower jaw dental arc.

According to another preferred embodiment of the registration system according to the invention, it is provided that the bite carrier comprises a data memory for storing registration data, or that a data memory device for storing registration data can be disposed on the bite carrier. This makes it possible that after the jaw joint registration or hinge axis determination on the patient has been carried out, some or all of the registration data can be stored in the data memory of the bite carrier. Subsequently, solely and alone the bite carrier, with the tooth impressions disposed on it, as the bite key, as well as the data contained in the data memory device unit, particularly concerning the patient hinge axis location, must be passed on to the dental technician laboratory, for example.

Thus, the dental technician is able, solely on the basis of the content of the bite carrier, with the data memory device disposed in it, to place jaw models of the patient into the assembly stand or into the articulator, in the correct position and location. In this way, transferring and passing on the data concerning the geometry of the patient's jaw joint, for example to the dental technician, can be simplified and accelerated in almost revolutionary manner as compared with the state of the art. At the same time, the error sources present in the state of the art are reduced or eliminated, and furthermore, costs can be saved to a significant extent.

In this manner, furthermore, not only the data concerning the patient hinge axis location, but instead, all the data relating to the complete jaw geometry of the patient, for example, can be stored in the data memory of the bite carrier. The bite carrier with the dental arc impression(s) disposed on it therefore, in itself, and without any other aids or documents, forms the complete and perfect documentation of the entire patient jaw geometry and all relevant data relating to the jaw geometry. This is not only of decisive advantage for the transfer of the jaw geometry to the dental technology laboratory, for example, but furthermore also opens up decisive new fields of use and simplifications, for example but by no means exclusively also in forensics.

According to another embodiment of the registration system according to the invention, the articulator is a modified but otherwise essentially conventional articulator or its upper part. This means, in other words, that the assembly stand in which the positioning of the lower jaw model of the patient relative to the hinge axis of the assembly stand takes place, on the basis of the data concerning the patient hinge axis location relative to the coupling device of the bite carrier, is essentially identical with an articulator or, at the same time, that the assembly stand represents the upper part of this articulator. In this manner, replacement of the assembly stand upper part with a separate articulator upper part, which is otherwise necessary, and, if applicable, additional assembly of articulator joint boxes after the model and geometry transfer to the assembly stand can be eliminated.

This embodiment of the registration system according to the invention is implemented, in the simplest case, in that an otherwise essentially conventional articulator is provided with a coupling accommodation for accommodating the coupling device of a bite key, whereby means for adjustment, precision adjustment, and fixation of the spatial relative position of the articulator hinge axis relative to the articulator coupling accommodation (or vice versa) are additionally provided on the articulator.

These adjustment means can be, according to other preferred embodiments of the invention, articulator joints or articulator joint sockets that can be adjusted relative to an articulator assembly plate, for example manually or also by means of servomotors.

Thus, the bite carrier can simply be directly attached to the coupling accommodation of the articulator, and the articulator hinge axis, before or afterwards, can be brought into the same spatial relative position with regard to the articulator hinge axis, relative to the articulator coupling device, as it corresponds to the relative position between bite carrier coupling device and patient hinge axis previously determined on the patient.

The invention furthermore relates to a connection device for releasably connecting a jaw adapter with a measurement carrier or with an intermediate adapter, particularly for jaw joint registration. The measurement carrier can particularly be a measurement arc for contact-free jaw registration; the intermediate adapter is particularly provided for connecting the jaw adapter to a related bite carrier.

According to the invention, the connection device is characterized in that it comprises a coupling magnet disposed in a magnetic coupling region of the connection device, for coupling the connection device with the connection accommodation. Preferably, in this connection, the coupling magnet can be moved out of the connection region—to separate the connection device from the connection accommodation—at an angle relative to the main magnetic force direction, preferably in a perpendicular direction relative to the main magnetic force direction.

The magnetic connection device particularly possesses the advantage that in this manner, extensively automatic engagement of the jaw adapter on the measurement carrier, or on the intermediate adapter, is possible. In this connection, this engagement can take place practically without any additional effect of force, particularly without any external effect of force, and therefore error sources due to accidental maladjustment can be eliminated.

Separation of the magnetic coupling between the connection device and the connection accommodation, for example of the intermediate adapter or measurement carrier, by means of moving the coupling magnet out at an angle relative to the main magnetic force direction—preferably in a perpendicular direction relative to the main magnetic force direction—is particularly advantageous in that in this way, the coupling magnet can be temporarily removed from the connection region with a minimal activation force.

In this way, the magnetically initiated or held connection can be very easily separated—again with the least possible external effect of force—without error-inducing reaction forces occurring because of the separation process.

Finally, the invention relates to a bite carrier for producing a bite key of a patient, particularly for use in jaw joint registration and model transfer. According to the invention, the bite carrier is characterized in that it is configured as an occlusal tray, whereby the occlusal tray comprises an occlusal bite fork for accommodating a bite key, as well as a cuff that can be releasably connected with the bite fork, to support the bite key.

This allows producing a bite key—and, if applicable, carrying out a jaw joint registration—in such a form that the bite fork and the cuff are first of all connected with one another, for example inserted into one another. In this way, the impression mass, which is still in paste form, is effectively prevented from flowing away to the side when the bite key is produced. After the impression mass has hardened, the cuff can be separated from the bite fork. In this manner, the bite key, now disposed on the bite fork in the form of the hardened impression mass, can be easily and freely processed or cut, accessible from all sides.

In the following, the invention will be explained in greater detail, using drawings that merely represent exemplary embodiments.

BRIEF DESCRIPTION OF THE DRAWINGS

These show:

FIG. 1 the lower jaw adapter with para-occlusal registration aid, occlusal bite fork, and measurement arc of an embodiment of a registration system according to the invention, in an isometric representation;

FIG. 2 in a representation corresponding to FIG. 1, the para-occlusal registration aid according to FIG. 1, with the related connection device;

FIG. 11 in an isometric representation corresponding to FIG. 1, the measurement arc and occlusal bite fork according to FIG. 1, with bite carrier cuff, ready for occlusal registration;

FIG. 12 in a representation corresponding to FIGS. 1 and 11, the bite carrier according to FIGS. 1 and 11, as well as its transfer to an assembly stand;

FIG. 13 in a representation and view corresponding to FIGS. 1 and 11, the measurement arc and para-occlusal bite registration according to FIGS. 1 and 2, ready for para-occlusal registration;

FIG. 14 in a representation and view corresponding to FIGS. 1, 11, and 13, the measurement arc, occlusal bite fork, and para-occlusal registration aid, during transfer of a bite key from the para-occlusal registration aid to the occlusal bite fork;

FIG. 15 in a representation and view corresponding to FIGS. 1, 11, 13, and 14, the intermediate adapter, occlusal bite fork, and para-occlusal registration aid, in the transfer of a bite key from the para-occlusal registration aid to the occlusal bite fork;

FIG. 16 in a representation and view corresponding to FIG. 15, the bite carrier according to FIGS. 1, 11, 12, 14, and 15;

DETAILED DESCRIPTION OF THE PREFERRED EMBODIMENTS

Figure 3:
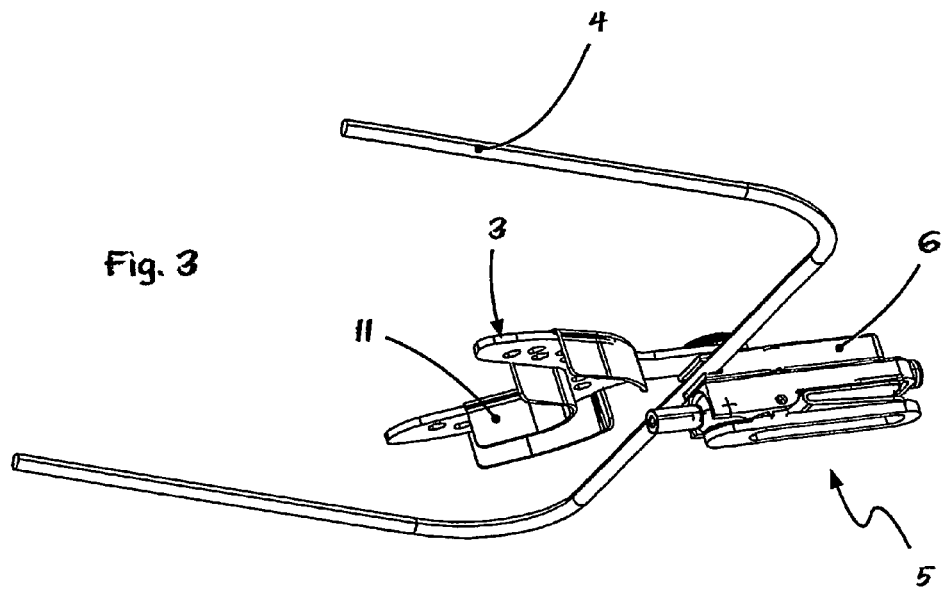
FIG. 3 in a representation corresponding to FIGS. 1 and 2, the lower jaw adapter and measurement arc of another embodiment of a registration system according to the invention.

FIG. 1 shows a lower jaw adapter 1 with a para-occlusal registration aid 2, an occlusal bite fork 3, as well as a measurement arc 4 for an embodiment of a registration system according to the invention, in an isometric representation; FIG. 2 shows the para-occlusal registration aid 2 according to FIG. 1, with the related connection device 5, separately once again, with the ball joint furthermore shown separately, so that they can be recognized more easily.

In this connection, the para-occlusal registration aid 2 serves to connect the lower jaw adapter 1, which here comprises connection device 5, intermediate adapter 6, and para-occlusal registration aid 2, as well as the measurement arc 4 here disposed on the lower jaw adapter 1 by means of the intermediate adapter 6, with the measurement markers 7, for the purpose of contact-free jaw joint registration and hinge axis determination with the dental arc (not shown) of the lower jaw of a patient.

Thus, a defined spatial relative relationship between the dental arc of the lower jaw, the patient hinge axis 8 of the patient, spatially assigned to this dental arc, the lower jaw adapter 1, as well as the measurement arc 4 with the measurement markers 7, is produced on the basis of the connection of the para-occlusal registration aid 2 with the dental arc of the lower jaw of the patient.

If now, for example, the location of the patient hinge axis 8 relative to the measurement markers 7 is determined by means of optical image follow-up and digital image processing of the images of the measurement markers 7 during a lower jaw movement of the patient, then in this way, the spatial location of the patient hinge axis 8 is first of all known relative to the measurement markers 7 and thus also to the measurement arc 4. However, the measurement arc 4 possesses a geometry that is also known, as well as known dimensions, whereby the measurement arc 4 is connected, in spatially precisely defined manner, first of all, with the lower jaw adapter 1—by means of the intermediate adapter 6—and furthermore, also with a coupling accommodation 9 that is disposed on the top of the intermediate adapter 6, with reference to the drawing.

The occlusal bite fork 3, in turn, can be connected with the lower jaw adapter 1, on the coupling accommodation 9, by means of its coupling device 10, also in spatially precisely defined manner.

This means, in other words, that subsequent to the contact-free hinge axis determination, the spatial location of the patient hinge axis 8 relative to all the components of the lower jaw adapter 1, and in this connection, also particularly relative to the coupling accommodation 9 on the lower jaw adapter 1, is known. Subsequent to the hinge axis determination, the occlusal bite fork 3 can therefore be connected, by means of its coupling device 10, with the coupling accommodation 9 of the lower jaw adapter 1, which continues to be positioned on the lower jaw dental arc of the patient, without any change, by way of the para-occlusal registration aid 2, whereby at the same time, an impression of the lower jaw row of the patient's teeth can be produced in the impression mass (not shown) applied to the underside of the occlusal bite fork 3.

Subsequent to this, not only the spatial relative position of the lower jaw row of the patient's teeth (on the basis of the impression of the patient's lower jaw stored on the occlusal bite fork 3 by means of the impression mass) but also the spatial relative position of the patient hinge axis 8 (on the basis of the geometrically defined chain of the measurement markers 7 by way of the measurement arc 4, the intermediate adapter 6, the coupling accommodation 9, all the way to the coupling device 10) relative to the occlusal bite fork 3 are known.

In other words, this means that all the information required to reproduce the patient hinge axis relative to the lower jaw dental arc is now coded merely in relation to the lower jaw bite fork 3. Thus, the absolute spatial position of the hinge axis 8 can be easily indicated, in precisely reproducible manner, for any desired given absolute spatial position of the lower jaw bite fork, i.e. for any desired given spatial position of the coupling device 10 of the lower jaw bite fork 3—using the data determined with regard to the spatial location of the patient hinge axis relative to the lower jaw bite fork 3, i.e. to its coupling accommodation 10.

Figure 17:
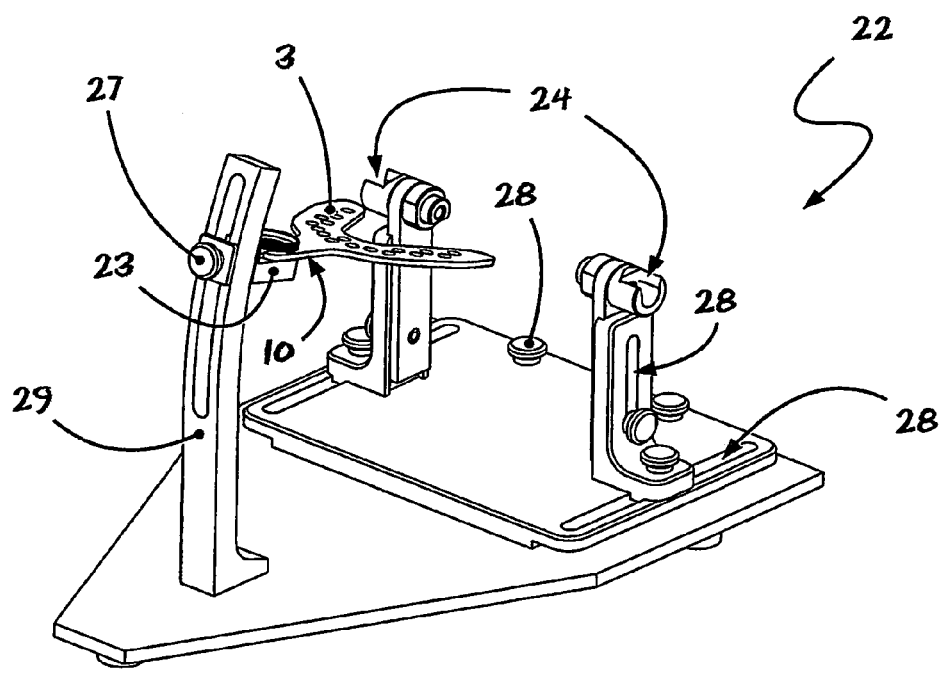
FIG. 17 in an isometric representation, an assembly stand of an embodiment of a registration system according to the invention, in a front view.
Figure 18:
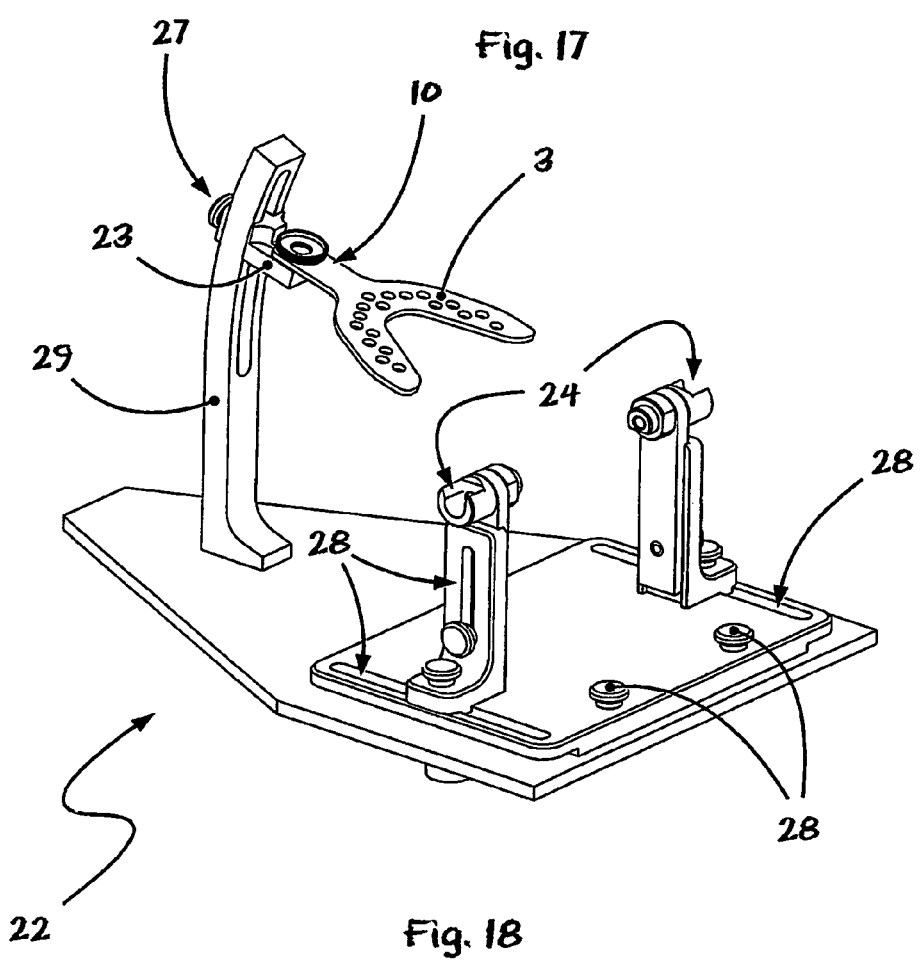
FIG. 18 in a representation corresponding to FIG. 17, the assembly stand according to FIG. 17, in a rear view.

This relationship particularly applies even if the lower jaw bite fork 3 is placed on a corresponding coupling accommodation of an articulator or articulator assembly stand, for example, by means of its coupling device 10, as shown in FIGS. 12, 17, and 18, for example. As soon as the lower jaw bite fork with the bite key disposed on it in the form of the lower jaw tooth impressions has thus been connected, in the articulator or assembly stand, by means of connecting its coupling device 10 with the coupling accommodation of the articulator or assembly stand, the precise spatial position of the patient hinge axis 8 can thus be indicated also in the articulator or assembly stand, on the basis of the measured data concerning the spatial location of the patient hinge axis relative to the coupling accommodation 10 of the lower jaw bite fork 3, and can be reproduced accordingly in the assembly stand.

Figure 4:
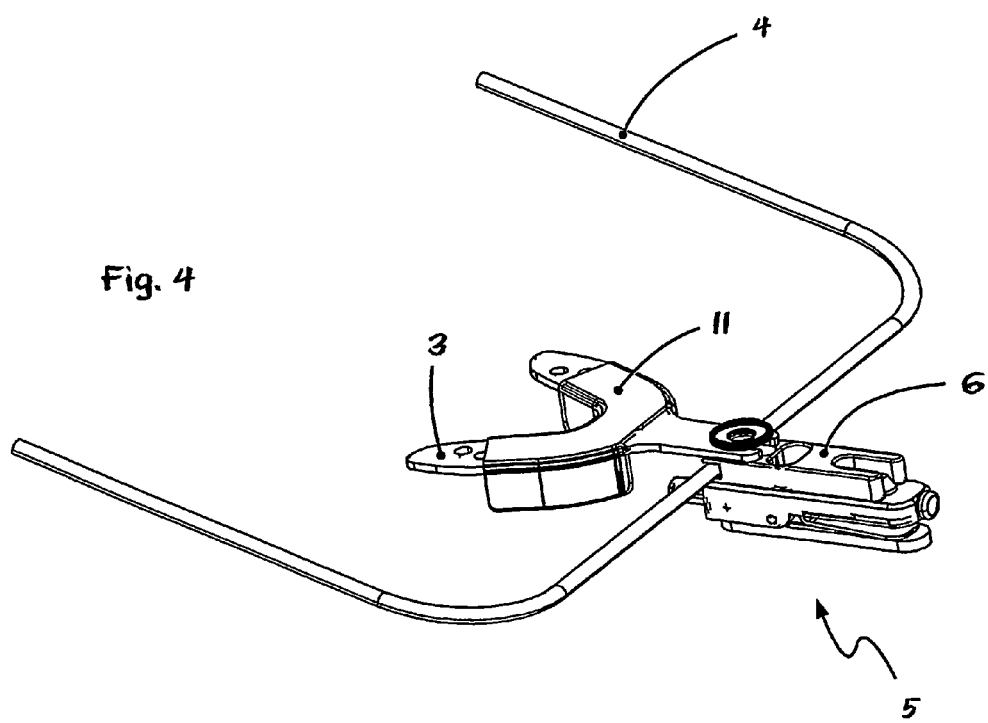
FIG. 4 in a representation corresponding to FIGS. 1 to 3, the lower jaw adapter and measurement arc according to FIG. 3, in another view.
Figure 5:
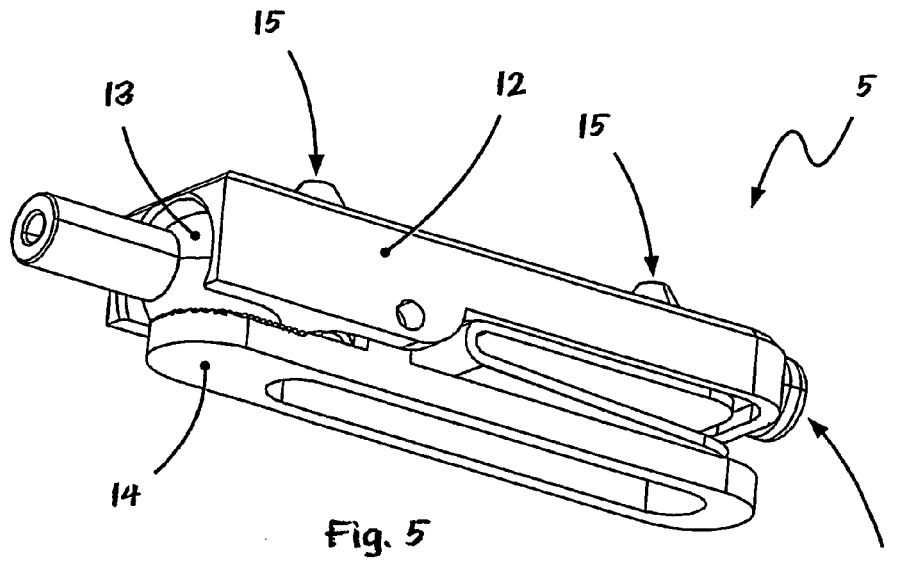
FIG. 5 in a perspective representation, the connection device of the lower jaw adapter according to FIGS. 3 and 4 in an enlarged view.
Figure 6:
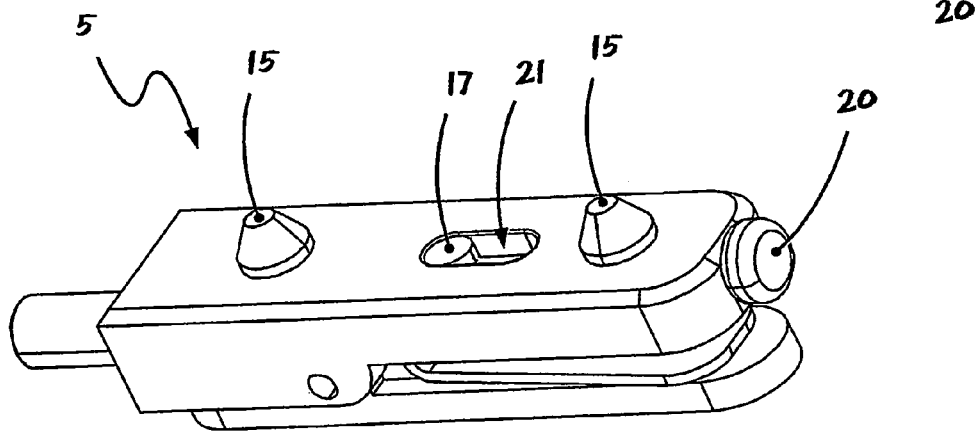
FIG. 6 in a representation corresponding to FIG. 5, the connection device according to FIG. 5.
Figure 7:
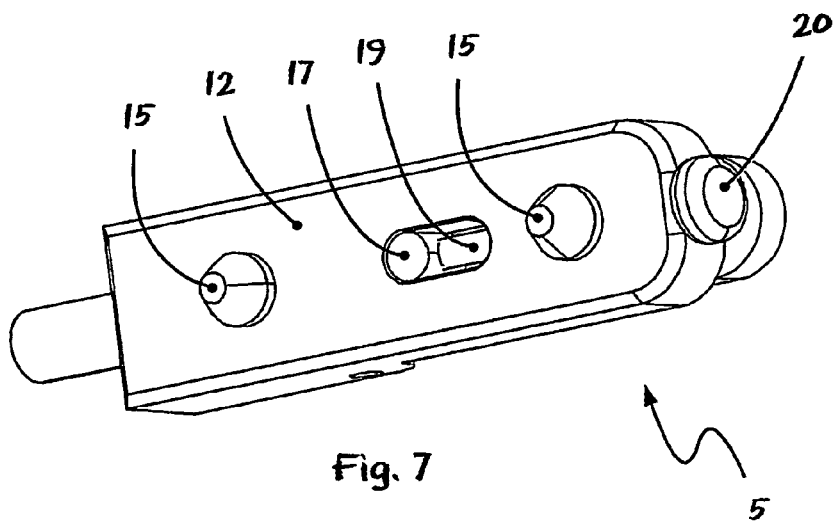
FIG. 7 in a representation corresponding to FIGS. 5 and 6, the connection device according to FIGS. 5 and 6, in a top view.

FIGS. 3 and 4, each in an isometric view that essentially corresponds with the representation of FIGS. 1 and 2, show the lower jaw adapter and the measurement arc of another embodiment of a registration system according to the invention. In this connection, for the sake of a better overview, in the representations of FIGS. 3 and 4, both the carrier brackets disposed on the measurement arc 4, with the measurement markers 7 disposed on them, and the tooth contact surface of the para-occlusal registration aid 2 according to FIG. 1 have been left out, i.e. not shown.

In contrast to FIGS. 1 and 2, first of all the cuff 11 that has been set onto the occlusal bite fork 3 can be seen in FIGS. 3 and 4. The cuff 11 prevents the impression mass, which is still in paste form, from flowing away to the side when a bite impression of the corresponding row of the patient's teeth is being produced. After the impression mass has hardened, the cuff 11 can then be pulled off the bite fork 3. Subsequently, the bite key, which is now disposed on the bite fork 3 in the form of the hardened impression mass, can easily be worked on, for example trimmed, being accessible from all sides.

The lower jaw adapter 1 shown in FIGS. 3 and 4 furthermore differs from the lower jaw adapter shown in FIG. 1 by means of the structure of the intermediate adapter 6 that serves to couple the occlusal bite fork 3 with the connection device 5 of the para-occlusal registration aid 2 (not shown here), as well as with the measurement arc 4.

Figure 8:
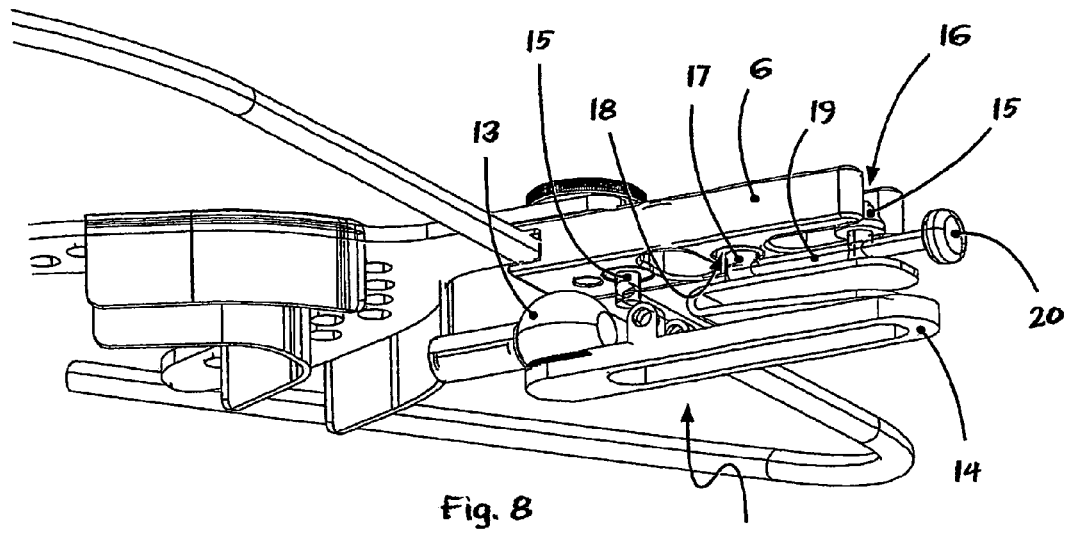
FIG. 8 in a schematic perspective representation, the lower jaw adapter and measurement arc according to FIGS. 3 and 4, without the housing of the magnetic connection device.
Figure 9:
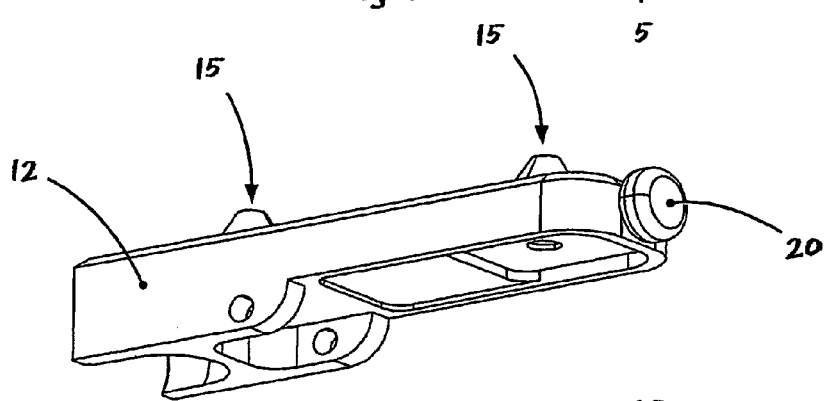
FIG. 9 in a representation and view corresponding to FIG. 8, the magnetic connection device for the lower jaw adapter according to FIG. 8.
Figure 10:
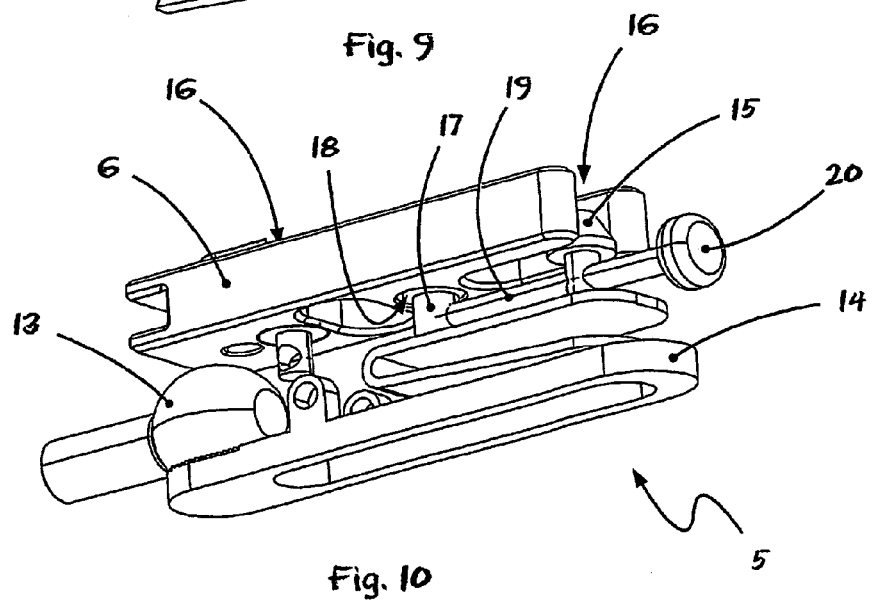
FIG. 10 in a representation and view corresponding to FIGS. 8 and 9, the lower jaw adapter according to FIGS. 3 to 7 without the housing of the magnetic connection device.

In FIGS. 5 to 10, the connection device 5—and, in this connection, in FIGS. 8 and 10, additionally also the intermediate adapter 6 coupled with the connection device 5, in each instance—according to the embodiment of the lower jaw adapter 1 from FIGS. 3 and 4 is shown once again in an enlarged view in each instance, whereby in FIGS. 8 and 10, for the sake of better recognition of the function of the connection device 5, the corpus 12 of the connection device 5 according to FIG. 9 was masked out. Particularly in FIGS. 5 to 7, first of all, the configuration of the connection device 5 for connecting the para-occlusal registration aid with the intermediate adapter 6, not shown in FIGS. 5 to 7, can be seen, along with the adjustment possibility, structured as a ball joint 13 with spring clamp 14, of the para-occlusal registration aid relative to the connection device 5. The ball joint 13 particularly serves for approximate manual adjustment of the lower jaw adapter 1 with the measurement arc 4 disposed in it, in advance of the hinge axis determination.

For a spatially precisely defined and reproducible contact and connection of the connection device 5 with the intermediate adapter 6, the connection device 5 shown in FIGS. 5 to 10 furthermore first of all has two centering tips 15 firmly connected with the corpus 12 of the connection device. When the connection device 5 and the intermediate adapter 6 are joined together, the centering tips 15 come to lie on the intermediate adapter 6 in corresponding recesses 16 formed to be precisely complementary in shape (see FIGS. 8 and 10) and thus assure a precisely reproducible connection, with shape fit and free of play, between connection device 5 and intermediate adapter 6.

The actual fixation of the connection between connection device 5 and intermediate adapter 6 is taken over, in this connection, by a coupling magnet 17 disposed in the connection device 5. The coupling magnet 17 disposed in the connection device 5 has a corresponding magnet counterpart (not shown) composed of magnetically active or magnetically activatable material, which is disposed in a corresponding recess 18 of the intermediate adapter 6; see FIGS. 8 and 10, in particular, in this regard.

Thus, connection device 5 and intermediate adapter 6 can be connected with one another practically free of external activation or reaction forces, in that they are simply brought into contact with one another. In this connection, the reciprocal attraction force of the coupling magnet 17 and the magnet counterpart 18, together with the centering tips 15 of the connection device 5 and the recesses 16 in the intermediate adapter 6 assigned to them, assure that a play-free connection, fixed in all three spatial directions, between connection device 5 and intermediate adapter 6 is present.

If now the connection between connection device 5 and intermediate adapter 6 is supposed to be released again, then this can take place easily and practically free of reaction forces, thanks to a displacement device for the coupling magnet 17 that can be seen in FIGS. 5 to 10. The displacement device comprises a guide pin 19 that can be displaced axially in the corpus 12 of the connection device 5, as well as an activation handle 20 disposed on an axial end of the guide pin 19. The end of the guide pin 19 that lies opposite the activation handle 20 is firmly connected with the coupling magnet 17 of the connection device 5. Furthermore, the coupling magnet 17 is disposed to be movable along the axial direction of the guide pin, in a corresponding elongated hole 21 in the corpus 12 of the connection device 5, see FIG. 6.

In the views shown in FIGS. 5 to 8 and 10, the coupling magnet 17 is in its starting position, in each instance, in which the coupling magnet 17 comes to lie precisely on the magnet counterpart 18 of the intermediate adapter 6, as soon as connection device 5 and intermediate adapter 6 are laid against one another. To release the magnetic connection between connection device 5 and intermediate adapter 6, the coupling magnet 17 can now be removed from the connection region, in other words from its contact position on the magnet counterpart 18 of the intermediate adapter 6, by means of activating the guide pin 19 by pulling the activation handle 20 out of the corpus 12 of the connection device 5, perpendicular to the main magnetic force direction. This movement of the coupling magnet 17 out of the connection region, perpendicular to the main magnetic force direction, requires only a relatively minimal activation force, which is furthermore almost uniform over a long linear activation path.

Separation of the magnetic connection between connection device 5 and intermediate adapter 6 can thus take place almost free of reaction forces, thanks to the displacement device 19, 20, even if a comparatively strong coupling magnet 17 is used, which could be removed from its contact position on the magnet counterpart 18 of the intermediate adapter 6 only with the application of great separation forces, along the main magnetic force direction.

In particular, in this manner, the intermediate adapter 6 can be separated from the connection device 5 even then, by means of merely slight activation forces on the activation handle, as long as the connection device 5 is still connected with the patient's row of teeth by means of the para-occlusal registration aid 2. In this manner, it is possible to avoid the occurrence of undesirable distortions of the precise positioning of the para-occlusal registration aid 2 and of the connection device 5 relative to the dental arc and jaw of the patient, when the intermediate adapter 6 and the measurement arc 4 connected with it, for example, are taken off the connection device 5 of the para-occlusal registration aid 2.

FIGS. 11 and 12 symbolize, in a highly schematic abstraction, the course of the transfer of the jaw joint geometry, particularly the patient hinge axis location, to the occlusal bite fork 3 for the case of occlusal registration. In the occlusal registration, both for determining the hinge axis location according to FIG. 11—using the measurement arc 4 with the measurement markers 7—and for geometry transfer to the assembly stand 22 or articulator according to FIG. 12, the same occlusal bite fork 3 is used.

In this connection, first of all, according to FIG. 11, the spatial location of the patient hinge axis 8 relative to the occlusal bite fork 3, particularly relative to the coupling device 10 of the bite fork 3, is determined using the measurement arc 4 with the measurement markers 7 disposed on it, in contact-free manner, i.e. optically, as described above. Subsequent to the jaw joint registration or patient hinge axis determination, the bite fork 3, with the lower jaw tooth impression (not shown) disposed on it, can then be mounted in a corresponding articulator or assembly stand 22 according to FIG. 12, as a bite key, together with the related data set that describes the spatial relative position of the patient hinge axis 8 relative to the coupling device 10 of the bite fork 3.

This is symbolized in FIG. 12 in that the position of the patient hinge axis 8 is indicated in the assembly stand 22 shown in FIG. 12, by means of a dotted line. It can be seen that in the neutral position of coupling accommodation 23 and joint socket 24 of the assembly stand 22, the actual location of the hinge axis 8 of the patient (dotted line) does not yet agree with the hinge axis 25 of the assembly stand 22 (dot-dash line).

However, since the spatial relative position between the coupling device 10 of the bite fork 3 and the hinge axis 8 of the patient is precisely known on the basis of the jaw joint registration that was previously carried out, this spatial relative position between the coupling device 10 of the bite fork 3—i.e. between the coupling accommodation 23 of the assembly stand 22 connected with the coupling device 10—and the assembly stand hinge axis 25 can be precisely reproduced on the assembly stand 22, as well, by means of corresponding adjustment of the assembly stand 22.

This means, in other words, that the precise jaw joint geometry can be produced in the assembly stand 22 or articulator, merely on the basis of the placement of the bite fork 3 with the tooth impressions disposed on it as the bite key, taking into consideration the data concerning the patient hinge axis, and appropriate adjustment of the assembly stand 22 or articulator.

FIGS. 13 to 16 symbolize, analogous to the representation in FIGS. 11 and 12, the sequence of transfer of the jaw joint geometry, particularly of the patient hinge axis location 8, to the occlusal bite fork 3, but here for the case of para-occlusal registration. In the case of para-occlusal registration, first of all it is not the occlusal bite fork 3 that is used, as before, but rather the para-occlusal registration aid 2, to determine the patient hinge axis location 8 according to FIG. 13—again using the measurement arc 4 with the measurement markers 7. This has the particular advantage that during the registration, no kind of interference with the natural occlusion of the patient can occur.

After the spatial position of the patient hinge axis 8 relative to the para-occlusal registration aid 2 has thus been determined according to FIG. 13, this spatial/geometrical information must also be transferred to the occlusal bite fork 3. This transfer of the jaw joint geometry from the para-occlusal registration aid 2 to the occlusal bite fork 3 takes place either as shown in FIG. 14 or as shown in FIG. 15.

The difference between the method of procedure symbolized in FIG. 14 and the one in FIG. 15 merely lies in the fact that the geometry transfer according to FIG. 14 is carried out while the intermediate adapter 6, with the measurement arc 4 disposed on it, is still disposed on the connection device 5, while in the geometry transfer according to FIG. 15, the intermediate adapter 6, with the measurement arc 4 disposed on it, was first removed from the connection device 5 of the para-occlusal registration aid 2. In the case of the method of procedure symbolized in FIG. 15, another intermediate adapter 26, complementary in shape to the first intermediate adapter 6, along with the occlusal bite carrier 3 disposed on it, is then disposed on the connection device 5 of the para-occlusal registration aid 2, something that can again take place automatically, with magnetic initiation, and thus practically free of external forces, thanks to the magnetic connection 17, 18 of intermediate adapter 13 and connection device 5.

In this connection, at the same time, another impression of the dental arc of the lower jaw is produced in the impression mass (not shown) disposed on the underside of the occlusal bite fork 3—in addition to the impression disposed on the para-occlusal registration aid 2. Since the production of this impression—on the basis of the connection of the occlusal bite fork 3 by means of the coupling device 10 and the coupling accommodation 9 of the intermediate adapter 6 or 26—again takes place with a precisely defined and known geometric relative position of the occlusal bite fork 3 relative to the patient hinge axis 8, the same result is obtained with FIG. 16 as was previously explained on the basis of the representations of FIGS. 11 and 12.

This means, according to FIG. 16, in other words, that after the geometry transfer from the para-occlusal registration aid 2 to the occlusal bite fork 3 according to FIG. 14 or FIG. 15—taking into consideration the data concerning the spatial location of the patient hinge axis 8 relative to the coupling device 10 of the occlusal bite fork 3—again the entire geometric information concerning the hinge axis location of the patient can be reproduced merely by installing the occlusal bite fork 3 with the bite key disposed on it and the patient hinge axis data set into an assembly stand 22 or articulator equipped with a corresponding coupling accommodation, see FIG. 12.

Finally, in FIGS. 17 and 18, the assembly stand 22 already shown in FIG. 12, for reproduction of the jaw joint geometry, including an occlusal bite fork 3 already disposed on the assembly stand 22, is shown once again in an isometric front and rear view.

It can be seen that the occlusal bite fork 3 can be disposed on a corresponding coupling accommodation 23 of the assembly stand 22 by means of its coupling device 10, and can be attached by means of a knurled screw 27. In this connection, the coupling accommodation 23 of the assembly stand is disposed on the assembly stand 22 to correspond in shape to the coupling accommodation 9 of the lower jaw adapter 1, i.e. of the intermediate adapter 6, 26, and thus allows precise, spatially defined, and reproducible placement of the occlusal bite fork 3 in the assembly stand 22.

Since, as described above, the spatial location of the patient hinge axis 8 relative to the occlusal bite fork 3, i.e. relative to the coupling device 10 of the occlusal bite fork 3, is known after the hinge axis determination, the spatial hinge axis location in the assembly stand 22 relative to the coupling accommodation 23 of the assembly stand can also be brought precisely into agreement with the hinge axis 8 of the patient.

For this purpose, the joint sockets 24 of the articulator assembly stand 22 shown can be adjusted in all three spatial directions, by means of corresponding parallel guides 28, and can be fixed in place in the desired position.

Adjustment of the joint sockets 24 in accordance with the previously determined data concerning the patient hinge axis location 8 relative to the coupling device 10 of the occlusal bite fork 3, i.e. to the coupling accommodation 23 of the assembly stand, can take place, in this connection—as an example, but by no means exclusively—by means of corresponding measurement scales (not shown) disposed on the parallel guides 28 of the assembly stand.

Just as well, the assembly stand 22, or an articulator structured accordingly, which thus replaces the assembly stand, can also be equipped with servomotor adjustment devices for corresponding displacement of the joint sockets 24 in the required spatial dimensions. In such a case, it is sufficient to merely input the corresponding data into a control device for the servomotor adjustment devices of the assembly stand 22 or articulator, in order to allow it to automatically assume precisely the jaw joint geometry of the patient, particularly with regard to the spatial hinge axis location 8.

If the assembly stand 22 or articulator is additionally provided with a data interface, and the occlusal bite carrier 3 is additionally provided with a data memory device for storing the geometry data of the jaw joint, as well as also with a data interface, then the transfer of the geometry data from the occlusal bite carrier 3 to an assembly stand 22 or articulator equipped with servomotors can take place fully automatically. In this case, the occlusal bite carrier 3 merely has to be placed into the assembly stand 22 or articulator, and afterwards, the assembly stand 22 or articulator reads out the data concerning the jaw joint geometry completely independently, from the data memory device of the occlusal bite carrier 3, and subsequently precisely reproduces the jaw joint geometry of the patient by means of servomotor adjustment, also fully automatically.

As is also evident from FIGS. 17 and 18, the coupling accommodation 23 disposed on the assembly stand 22 for coupling on the bite carrier can be adjusted along a guide device 29 configured in arc shape, relative to the base plate of the assembly stand 22. In this connection, the center point of the arc formed by the guide device 29 coincides with the assembly stand hinge axis 25 (see FIG. 12) in its zero position, i.e. in its starting position before transfer of the jaw geometry of the patient to the assembly stand.

In this manner, the skull reference plane previously determined for the patient, as well as the patient-specific reference angle, can also be transferred to the assembly stand 22 or articulator. In this way, subsequent to the transfer of the jaw joint geometry according to the invention, in particular, full articulation, including the entire jaw joint geometry, in relation to the reference plane, for example including condyle path incline, Bennett angle, retrusion/surtrusion and/or immediate side shift, etc., can also take place.

In the end result, it therefore becomes clear that with the invention, the technology of the transfer of jaw models in relation to the hinge axis is decisively improved, expanded, and, at the same time, simplified. In this connection, the invention makes a high degree of modularization possible, along with significantly simplified and accelerated use, as well as particularly great precision in the determination and transfer of the jaw joint geometry of a patient to an assembly stand or articulator. At the same time, error sources are systematically eliminated, the apparatus expenditure is decisively reduced, and furthermore, effects of the apparatus on the patient are minimized.

The invention thus makes a contribution to improving jaw joint registration and transfer of jaw joint geometries and jaw models from the patient to an assembly stand or articulator that must be called revolutionary.

The invention claimed is:

1. Method for transfer of a jaw model of a patient in relation to a patient hinge axis, via a lower jaw adapter (1), to an articulator assembly stand (22) having an assembly stand hinge axis (25), the method comprising the following steps:
 a) placing impression mass on a lower-jaw-side tooth contact surface of the lower jaw adapter (1);
 b) connecting the lower jaw adapter (1) with the dental arc of the patient's lower jaw, via the impression mass, thereby producing an impression of the lower jaw row of teeth in the impression mass such that a lower jaw model of the patient is formed;
 c) carrying out a jaw joint registration with hinge axis determination, whereby the relative position between the patient hinge axis (8) and the lower jaw adapter (1) is determined;
 d) connecting a bite carrier (3) of the lower jaw adapter (1) with the lower jaw model of the patient, via the lower jaw tooth impression in the impression mass on the bite carrier (3);
 e) placing the bite carrier (3) and lower jaw model into the assembly stand (22) via connecting a bite carrier coupling device (10) of the bite carrier (3) with an assembly stand coupling accommodation (23) of the articulator assembly stand (22), the bite carrier coupling device (10) being connected to the bite carrier (3) and being complementary in shape with the assembly stand coupling accommodation (23) such that the bite carrier coupling device (10) can be connected with shape fit with the assembly stand coupling accommodation (23), the assembly stand coupling accommodation (23) being able to be disposed on the articulator assembly stand (22) in an adjustable, reproducible relative position with regard to the articulator hinge axis (25), and matching the relative spatial position of the assembly stand coupling accommodation (23) relative to the assembly stand hinge axis (25) of the articulator assembly stand (22) to the relative position between the patient hinge axis (8) and the lower jaw adapter (1) determined during registration, until agreement between the patient hinge axis (8) and the assembly stand hinge axis (25) is reached; and f) fixing the lower jaw model in place on the lower jaw assembly plate of the assembly stand (22).

2. Method according to claim 1, wherein the hinge axis determination in method step c) takes place via contact-free measurement of an opening movement of the lower jaw.

3. Method according to claim 2, wherein for contact-free measurement, a measurement carrier (4) is connected with the lower jaw adapter (1), whereby the measurement carrier (4) has marker elements (7) for contact-free position determination.

4. Method according to claim 3, wherein the connection of the measurement carrier (4) with the lower jaw adapter (1) takes place via a coupling accommodation (9) disposed on the measurement carrier (4), whereby the coupling accommodation (9) of the measurement carrier (4) is configured to be complementary in shape to the bite carrier coupling device (10) of the lower jaw adapter (1), and whereby the spatial position of the marker elements (7) of the measurement carrier (4), relative to the coupling accommodation (9) of the measurement carrier (4), is known.

5. Method according to claim 2, wherein the contact-free measurement takes place via optical image follow-up of the marker elements (7) carried out via at least one image-recording camera.

6. Method according to claim 5, wherein the contact-free measurement comprises digital image processing of the marker elements (7) recorded by the camera, whereby the digital image processing comprises at least one refocusing operation.

7. Method according to claim 1, wherein the hinge axis determination in method step c) comprises the determination of a skull-related reference plane and the related reference angle, whereby matching of the to the reference angle determined during registration additionally takes place in method step e) via adjustment of the reference angle position of the assembly stand coupling accommodation (23) as well as of the bite carrier (3) disposed on the coupling accommodation (23), together with the lower jaw model, with regard to a reference plane of the assembly stand (22).

8. Method according to claim 1, wherein the placement of bite carrier (3) and lower jaw model into the assembly stand (22) in method step e) as well as the matching of the spatial relative position of the assembly stand coupling accommodation (23) and the bite carrier (3) and lower jaw model disposed in it, takes place in method step e) via a lower jaw transfer arc, wherein the lower jaw transfer arc comprises two axis marking elements and, at the same time, the assembly stand coupling accommodation (23) forms a coupling accommodation for the bite carrier coupling device (10) of the bite carrier, whereby the spatial relative position between the connecting straight lines of the axis marking elements and the coupling device of the lower jaw transfer arc is adjustable on the lower jaw transfer arc, and can be fixed in place in agreement with the patient hinge axis location determined in method step c), and wherein the axis marking elements are connected with axis accommodation points of the assembly stand that lie on the hinge axis of the assembly stand.

9. Method according to claim 1, wherein the bite carrier of the lower jaw adapter (1) is configured as an occlusal bite fork (3).

10. Method according to claim 9, comprising the additional method steps:

c') applying impression mass also to the upper-jaw-side tooth contact surface of the bite carrier (3); and c'') producing an impression of the upper jaw dental arc in the impression mass disposed on the upper-jaw-side tooth contact surface of the bite carrier (3).

11. Method according to claim 1, wherein the bite carrier of the lower jaw adapter is configured as a para-occlusal registration aid (2).

12. Method according to claim 1, wherein the lower jaw adapter (1) comprises an occlusal bite fork (3) with a coupling device as a bite carrier, as well as a para-occlusal registration aid (2) with an intermediate adapter (6) —which has a coupling accommodation (9) for the bite carrier coupling device (10) of the occlusal bite fork (3) —whereby the para-occlusal registration aid (2) with the intermediate adapter (6) is used in method step c) for the hinge axis determination, and the spatial location of the patient hinge axis (8) relative to the coupling accommodation (9) of the intermediate adapter (6) is determined, the method comprising the additional method steps:

$c_1$) after the hinge axis determination, placement of the occlusal bite fork (3), via the intermediate adapter (6), on the para-occlusal registration aid (2) that is still disposed on the lower jaw of the patient, producing another impression of the lower jaw dental arc in an impression mass disposed on the tooth contact surface of the occlusal bite fork (3); and $c_2$) separating the occlusal bite fork (3) from the para-occlusal registration aid (2), as well as removing the occlusal bite fork (3) and the para-occlusal registration aid (2) from the lower jaw of the patient.

13. Method according to claim 1, wherein in method step c), the spatial position of the patient hinge axis (8) is determined both in a habitual intercuspidation position and in a therapeutic relative position between lower jaw and upper jaw that differs from the habitual one, the method comprising the additional method steps:

g) positioning an upper jaw model of the patient relative to the lower jaw model in the articulator assembly stand (22), as well as fixing the upper jaw model in place on an upper jaw assembly plate of the articulator assembly stand (22); and h) relatively displacing the upper jaw assembly plate together with the upper jaw model with regard to the lower jaw assembly plate together with the lower jaw model, until the therapeutic relative position has been reached.

14. A registration system comprising:

a jaw adapter (1) with a bite carrier (3) having a bite carrier coupling device (10);

an articulator assembly stand (22) having an assembly stand hinge axis (25);

a coupling accommodation (23) able to be disposed on the articulator assembly stand (22) in a reproducible relative position with regard to the assembly stand hinge axis (25); and a measurement carrier (4) for determining a patient hinge axis (8);

wherein a bite key of a patient can be disposed on the bite carrier (3);

wherein a jaw model of a patient including jaw hinge axis information can be transferred from the jaw adapter into the articulator assembly stand (22) via the jaw adapter (1) and the bite key when the bite key is on the bite carrier (3);

wherein the coupling accommodation (23) is complementary in shape to the bite carrier coupling device (10) and is connectable to the bite carrier coupling device (10) with shape fit;

wherein the jaw adapter (1) is a lower jaw adapter (1);

wherein the bite carrier (3) is a lower jaw bite carrier (3);

wherein the lower jaw adapter (1) can be connected with the measurement carrier (4);

wherein the jaw hinge axis information is relative to the bite carrier coupling device (10);

wherein, when the coupling accommodation (23) is disposed on the articulator assembly stand (22), a spatial position of the coupling accommodation (23) relative to the assembly stand hinge axis (25) is defined and reproducibly adjustable;

wherein the registration system can transfer a jaw model of a patient in relation to a hinge axis into the articulator assembly stand (22) via the lower law adapter (1) and via the bite key disposed on the bite carrier (3); and wherein the registration system is disposed for determination of the patient hinge axis (8) relative to the bite carrier coupling device (10).

15. Registration system according to claim 14, wherein the measurement carrier (4) has a coupling accommodation (9) that is complementary in shape to the bite carrier coupling device (10).

16. Registration system according to claim 14, wherein the coupling accommodation (23) is formed by a coupling accommodation of a lower jaw transfer arc that can be disposed on the articulator assembly stand (22) in a defined spatial relative position with regard to the assembly stand hinge axis (25), wherein the lower jaw transfer arc comprises two axis marking elements for the purpose of spatially defined placement of the lower jaw transfer arc on the articulator assembly stand (25), and wherein the spatial relative position between the connecting straight line of the axis marking elements and the coupling device of the lower jaw transfer arc is adjustable on the lower jaw transfer arc, and can be brought into agreement with the relative position between the patient hinge axis (8) and the bite carrier coupling device (10), and fixed in place on the lower jaw transfer arc.

17. Registration system according to claim 14, wherein the coupling accommodation (23) disposed on the assembly stand (22) for coupling on the bite carrier (3) is adjustable along a guide device (29) configured in arc shape, relative to an assembly plate of the assembly stand (22), and wherein the center point of the arc coincides with the assembly stand hinge axis (25) in a zero position.

18. Registration system according to claim 14, wherein the articulator assembly stand (22) is an articulator or an articulator upper part.

* * * * *